(12) United States Patent
Cartledge et al.

(10) Patent No.: US 6,554,791 B1
(45) Date of Patent: Apr. 29, 2003

(54) RAPID INFUSION SYSTEM

(75) Inventors: Richard G. Cartledge, Macon, GA (US); Hugh F. Smisson, III, Macon, GA (US); Jeffery O. Brown, North Logan, UT (US)

(73) Assignee: Smisson-Cartledge Biomedical, LLC, Macon, GA (US)

( * ) Notice: Subject to any disclaimer, the term of this patent is extended or adjusted under 35 U.S.C. 154(b) by 0 days.

(21) Appl. No.: 09/510,139

(22) Filed: Feb. 22, 2000

Related U.S. Application Data

(60) Provisional application No. 60/156,674, filed on Sep. 29, 1999.

(51) Int. Cl.$^7$ ............................................. A61M 31/00
(52) U.S. Cl. ........................................ 604/67; 604/131
(58) Field of Search .............................. 604/65, 66, 67, 604/131, 260, 251, 252, 253; 128/DIG. 12, DIG. 13

(56) References Cited

U.S. PATENT DOCUMENTS

| | | | |
|---|---|---|---|
| 3,985,133 A | 10/1976 | Jenkins et al. | 128/214 |
| 4,012,177 A | 3/1977 | Yakich | 417/477 |
| 4,187,057 A | 2/1980 | Xanthopoulos | 417/63 |
| 4,256,437 A | 3/1981 | Brown | 417/45 |
| 4,275,726 A | 6/1981 | Schael | 128/213 |
| 4,410,322 A | 10/1983 | Archibald | 604/153 |
| 4,475,901 A | 10/1984 | Kraegen et al. | 604/67 |
| 4,537,561 A | 8/1985 | Xanthopoulos | 417/63 |
| 4,685,902 A | 8/1987 | Edwards et al. | 604/153 |
| 4,747,826 A | 5/1988 | Sassano | 604/52 |
| 4,808,167 A | 2/1989 | Mann et al. | 604/151 |
| 4,856,972 A | 8/1989 | Van Benschoten et al. | 417/477 |
| 4,950,136 A | 8/1990 | Haas et al. | 417/477 |
| 5,061,241 A | 10/1991 | Stephens, Jr. et al. | 604/114 |
| 5,104,374 A | 4/1992 | Bishko et al. | 604/31 |
| 5,236,162 A | 8/1993 | Desjardins | 248/214 |
| 5,308,333 A | 5/1994 | Skakoon | 604/126 |
| 5,366,346 A | 11/1994 | Danby | 417/18 |
| 5,385,540 A | 1/1995 | Abbott et al. | 604/4 |
| 5,415,532 A | 5/1995 | Loughnane et al. | 417/411 |
| 5,419,684 A | 5/1995 | Struble et al. | 417/44.2 |
| 5,464,391 A | 11/1995 | DeVale | 604/67 |
| 5,482,446 A | 1/1996 | Williamson et al. | 417/474 |
| 5,573,502 A | 11/1996 | LeCocq et al. | 604/4 |
| 5,577,891 A | 11/1996 | Loughnane et al. | 417/53 |
| 5,746,719 A | 5/1998 | Farra et al. | 604/151 |
| 5,755,691 A | 5/1998 | Hilborne | 604/151 |
| 5,782,805 A | 7/1998 | Meinzer et al. | 604/131 |
| 5,840,068 A | 11/1998 | Cartledge | 604/131 |
| 5,928,196 A | 7/1999 | Johnson et al. | 604/153 |

FOREIGN PATENT DOCUMENTS

| | | |
|---|---|---|
| EP | 0120284 | 2/1984 |
| WO | WO 97/21456 | 6/1997 |

*Primary Examiner*—Manuel Mendez
(74) *Attorney, Agent, or Firm*—Sutherland, Asbill & Brennan, LLP

(57) ABSTRACT

A rapid infusion system for the intravenous delivery of fluids at standard and rapid flow rates. The system includes a pump assembly, a drive assembly to power the pump, and a fluid containment system that keeps the infused fluid out of direct contact with the pump assembly and that is preferably disposable and removable. In one embodiment the drive assembly includes a differential drive that interacts with more than one motor. In one embodiment, the pump assembly includes a roller pump and the pump chamber is a collapsible, preformed tube that is preferably attached to a pump cartridge frame. Optionally, the system includes a self-leveling drip chamber and the fluid containment system is disposable and includes a pump cartridge containing the drip chamber and the pump chamber, I.V. tubing, outlet infusion tubing, and a heater cartridge.

18 Claims, 19 Drawing Sheets

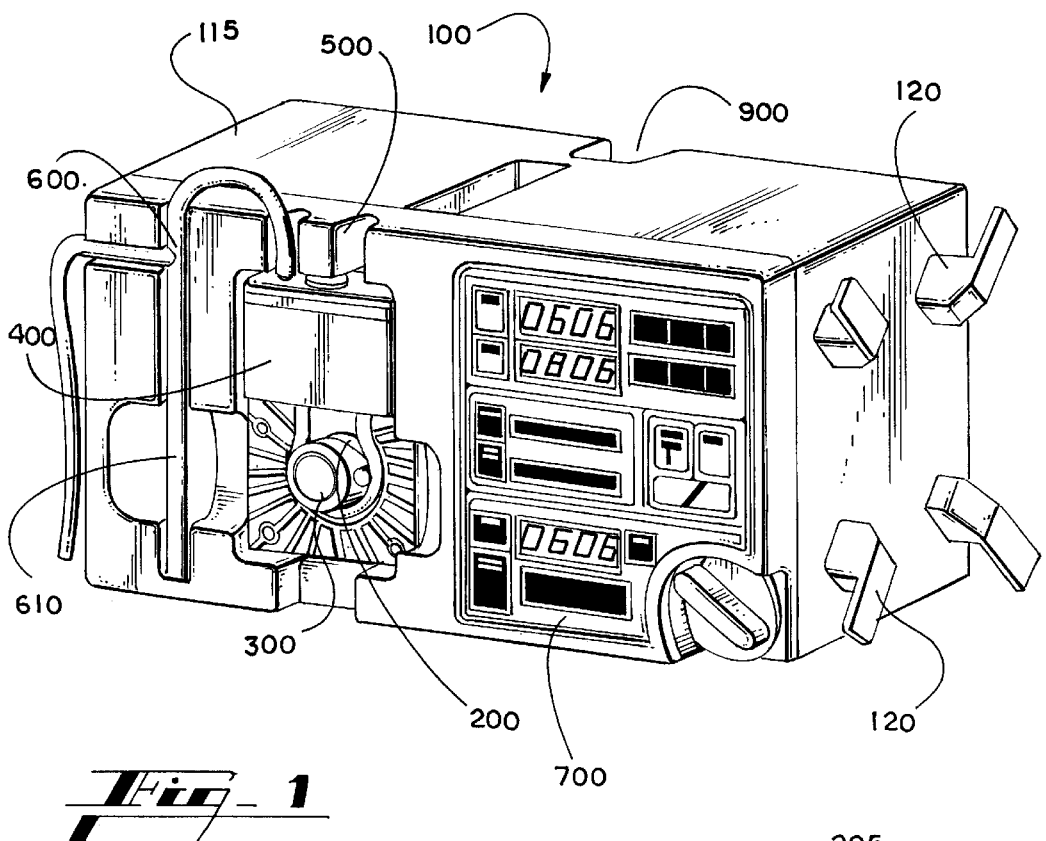
Fig_1
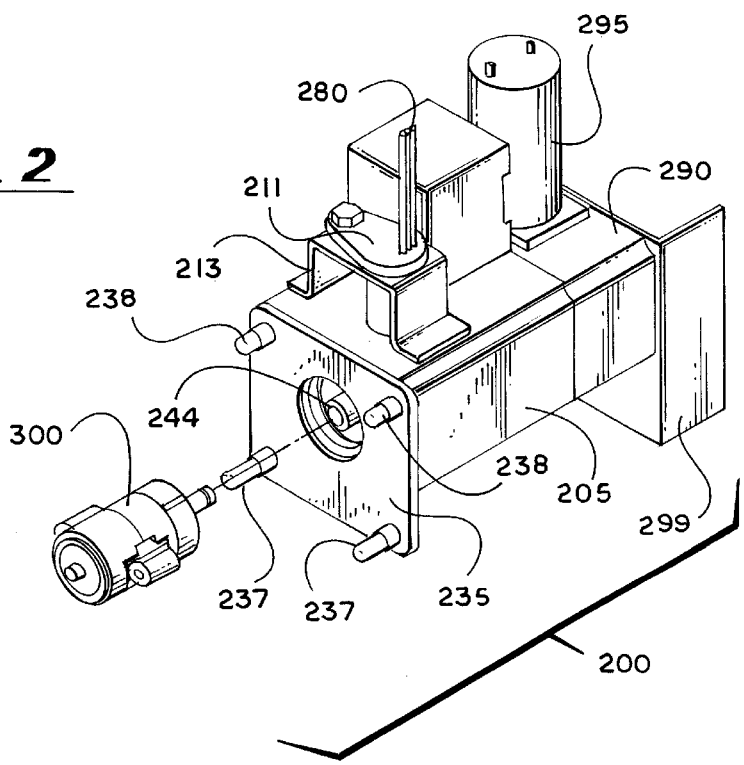
Fig_2

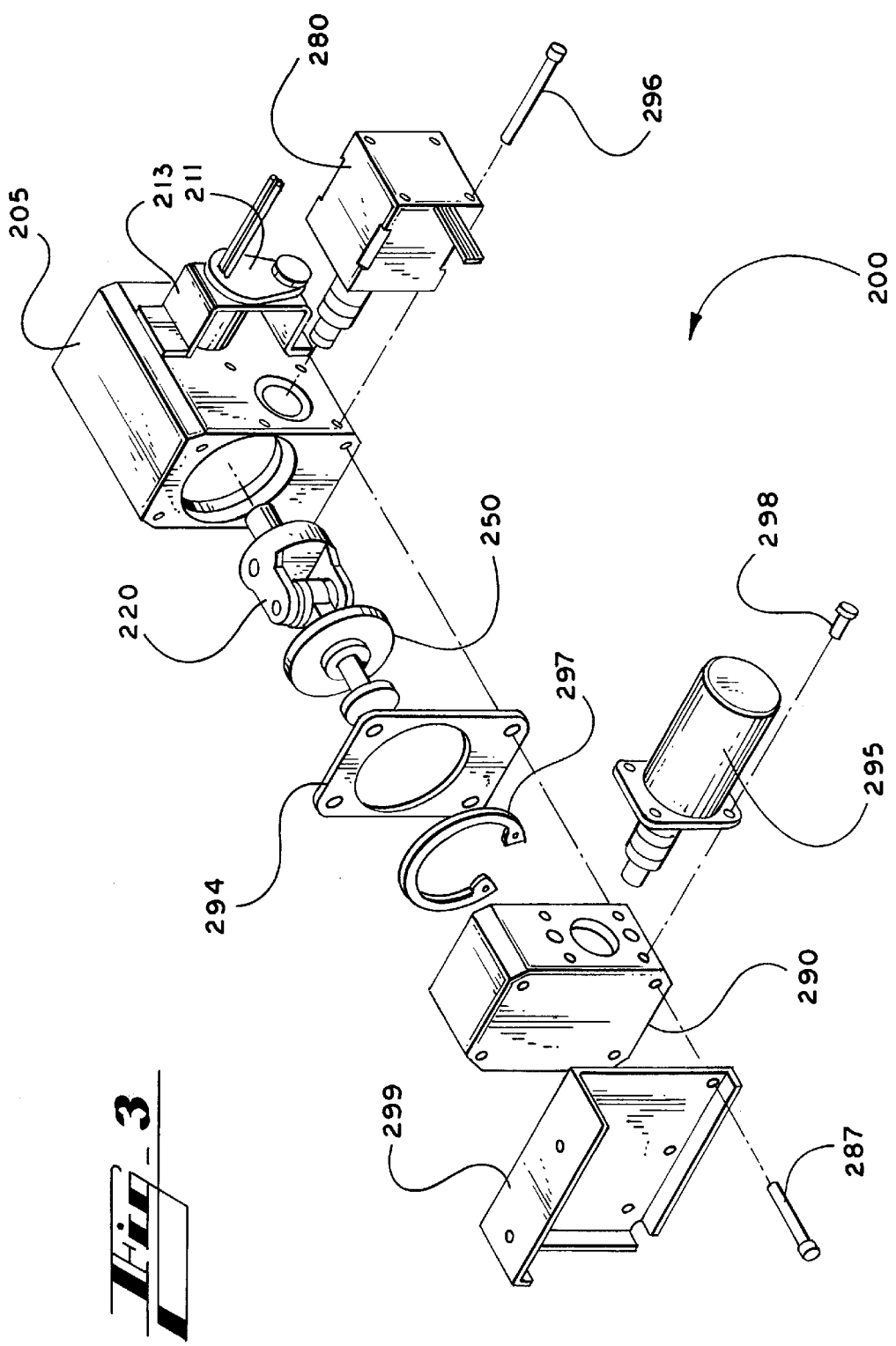

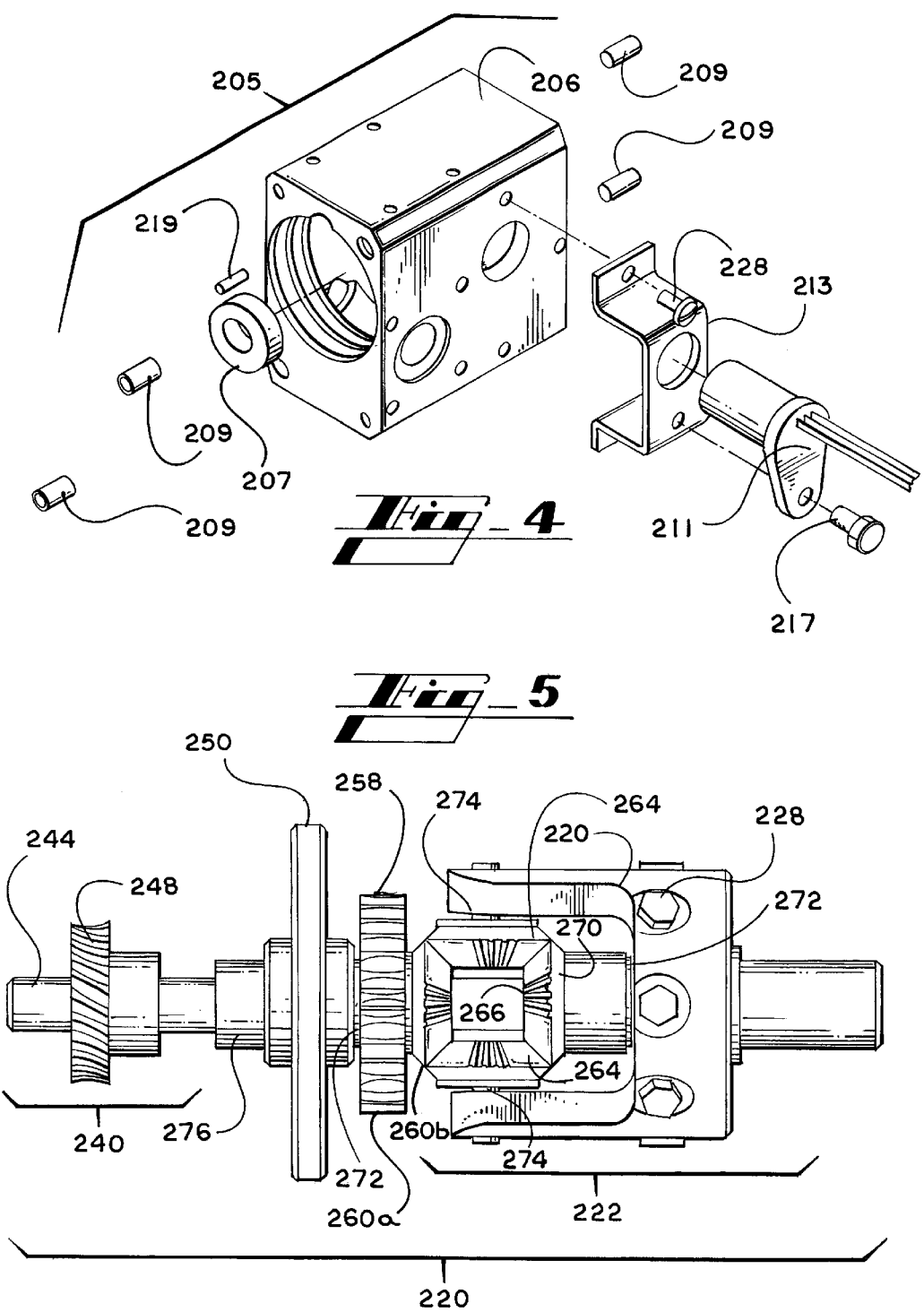

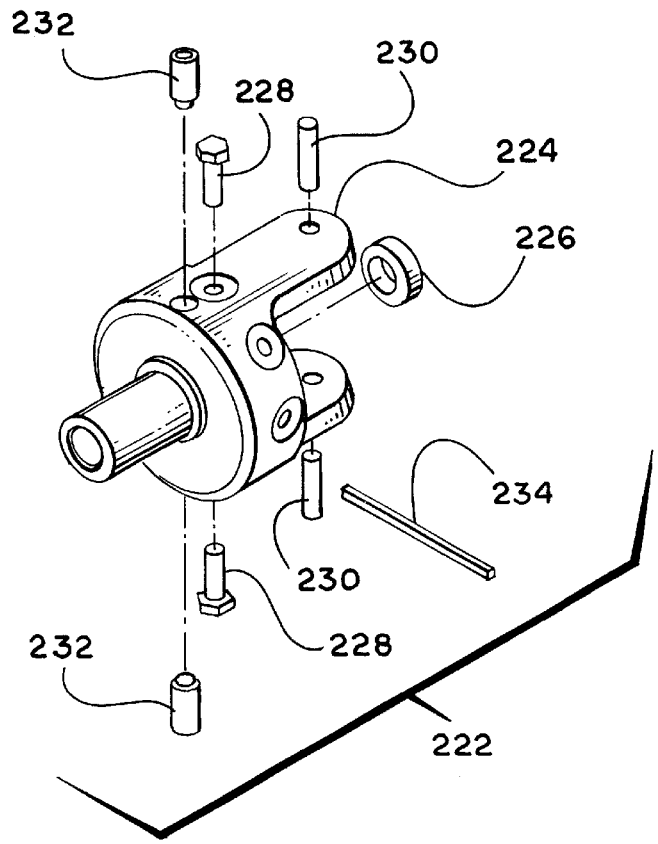
Fig_6
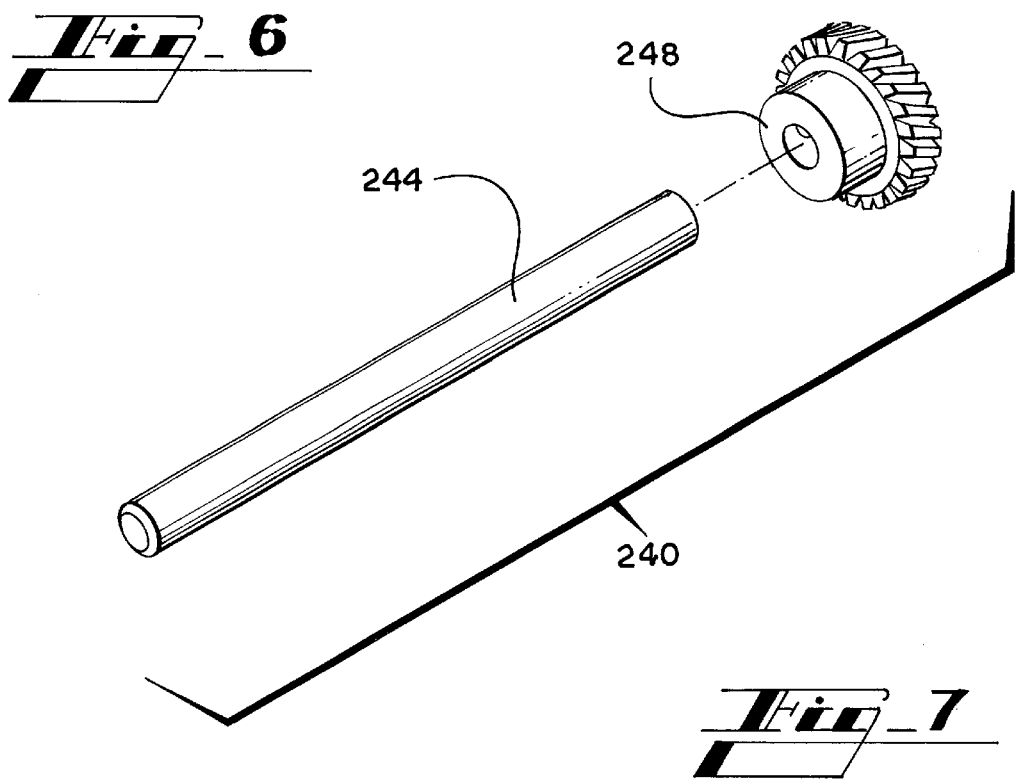
Fig_7

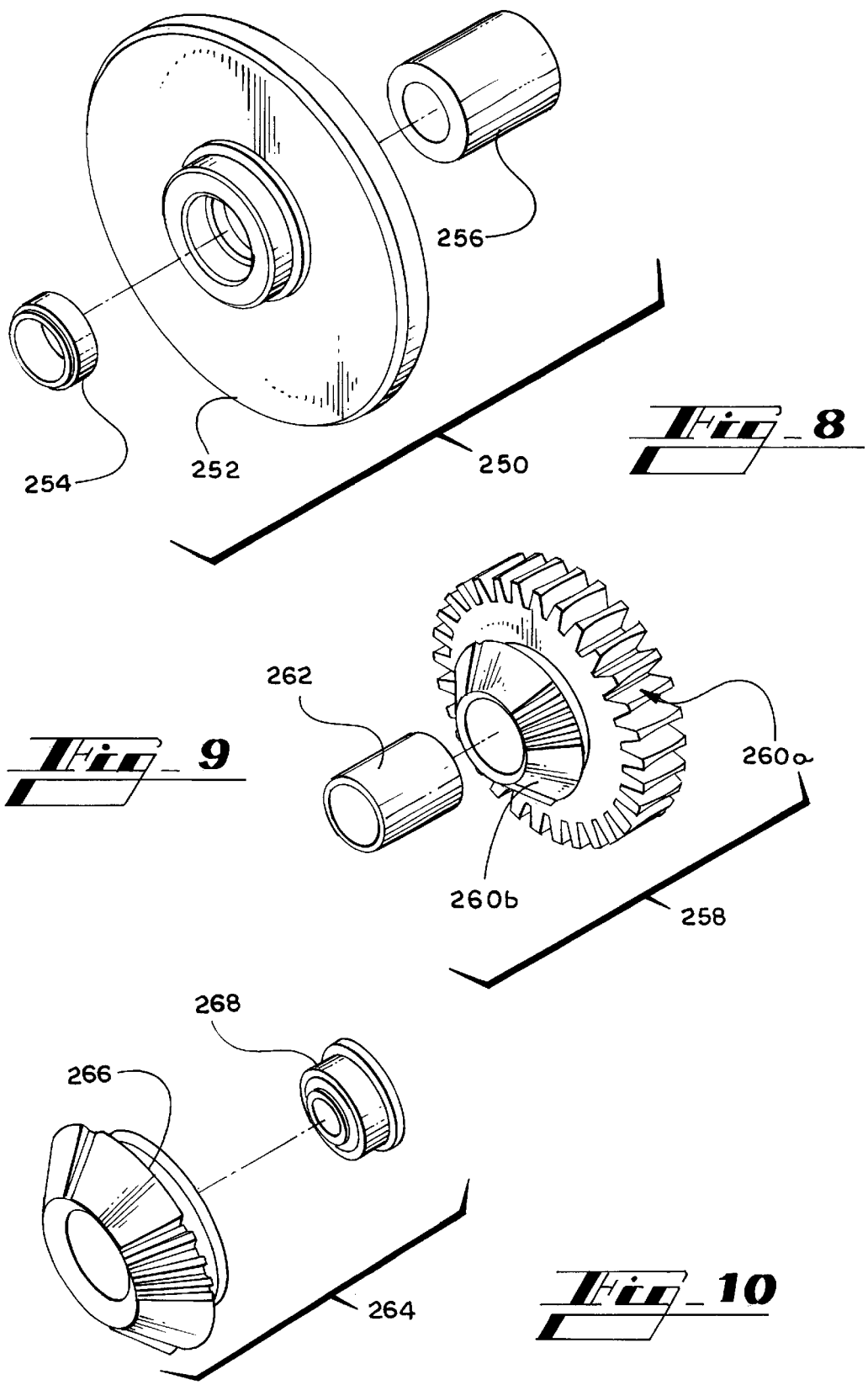

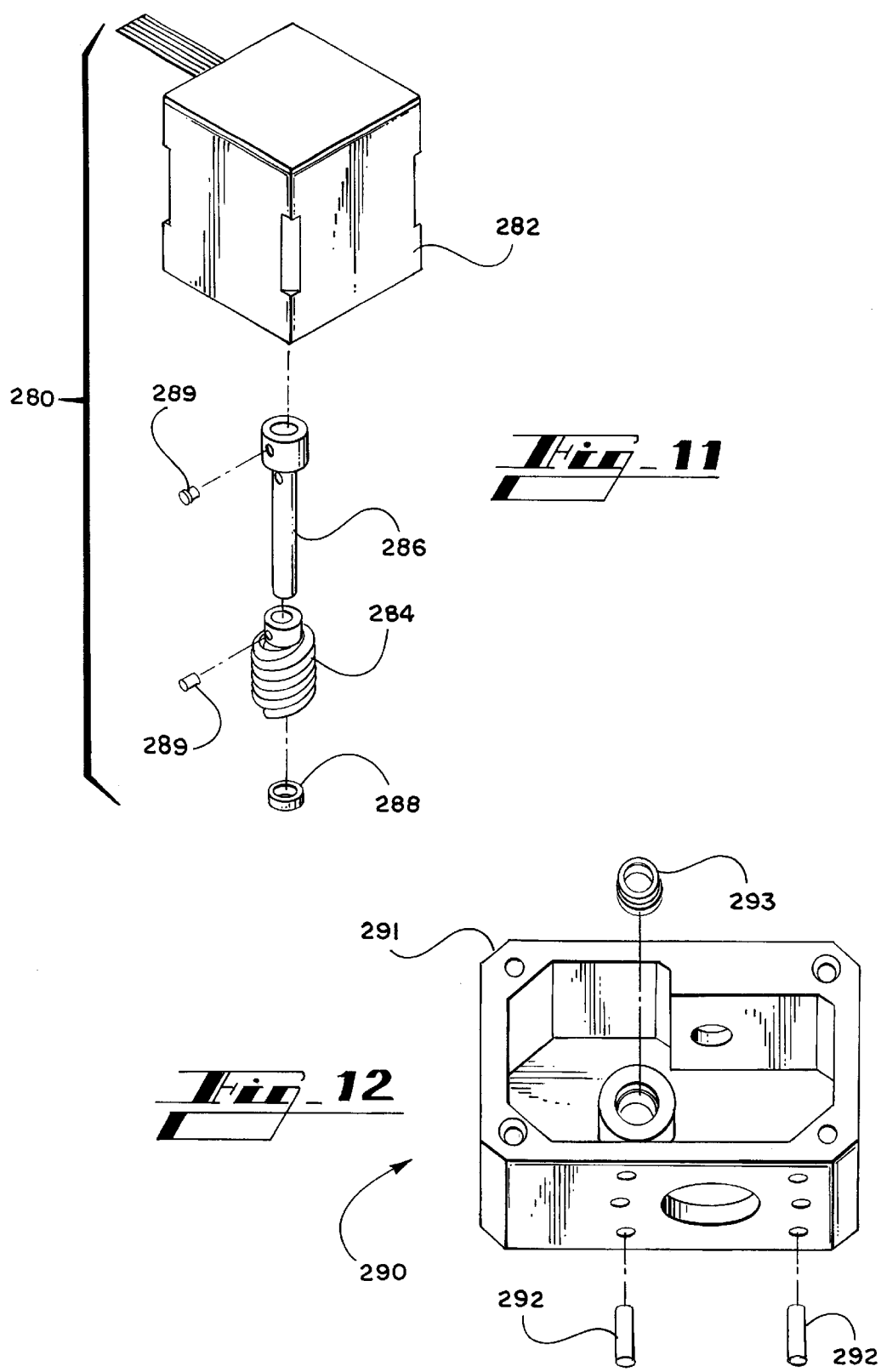

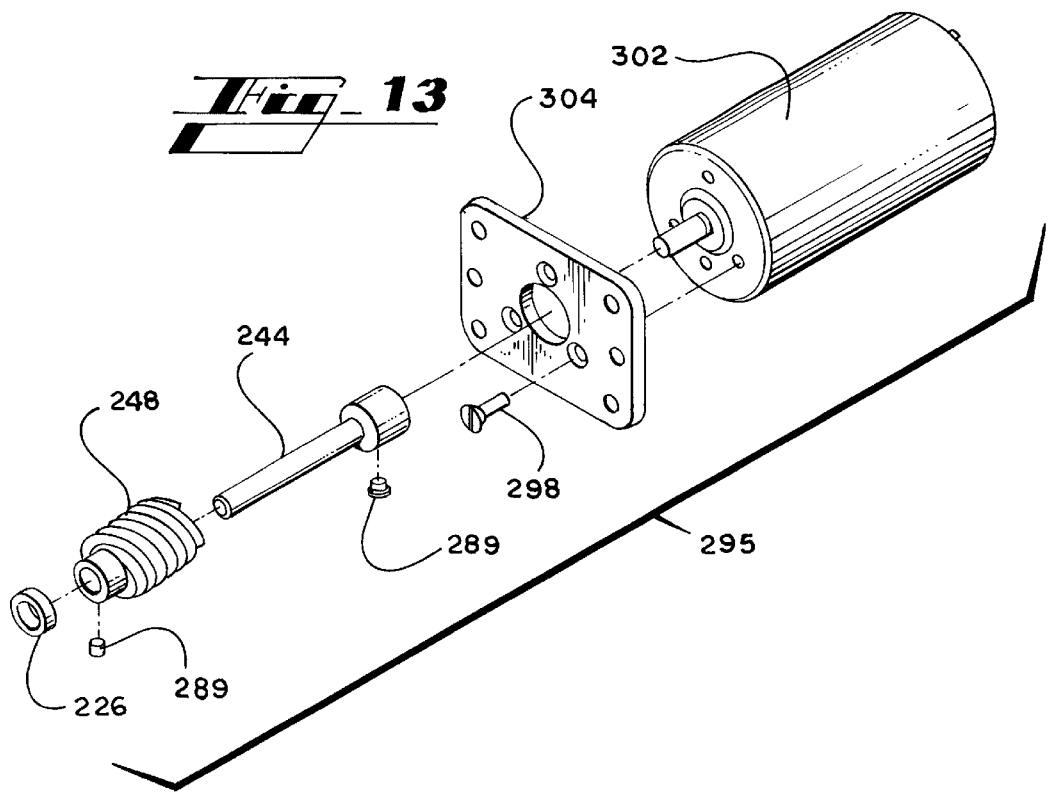
Fig_13
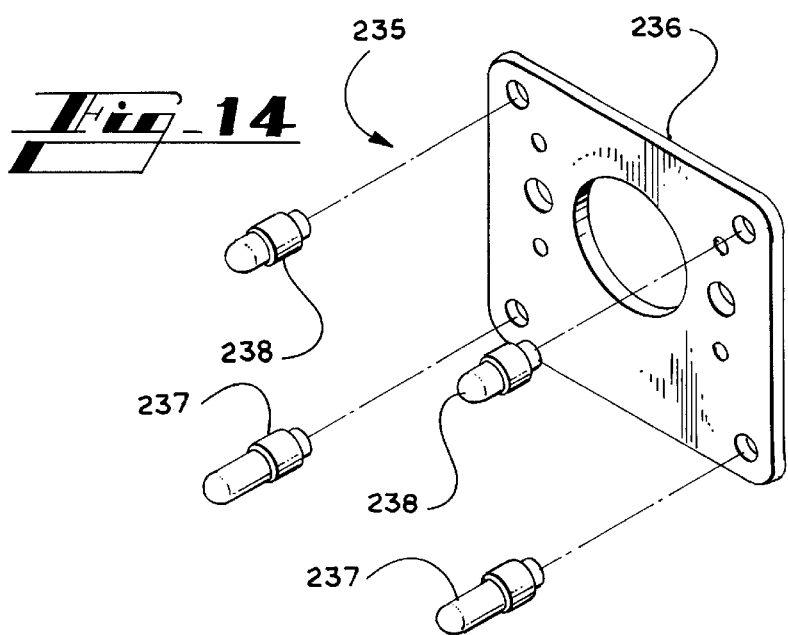
Fig_14

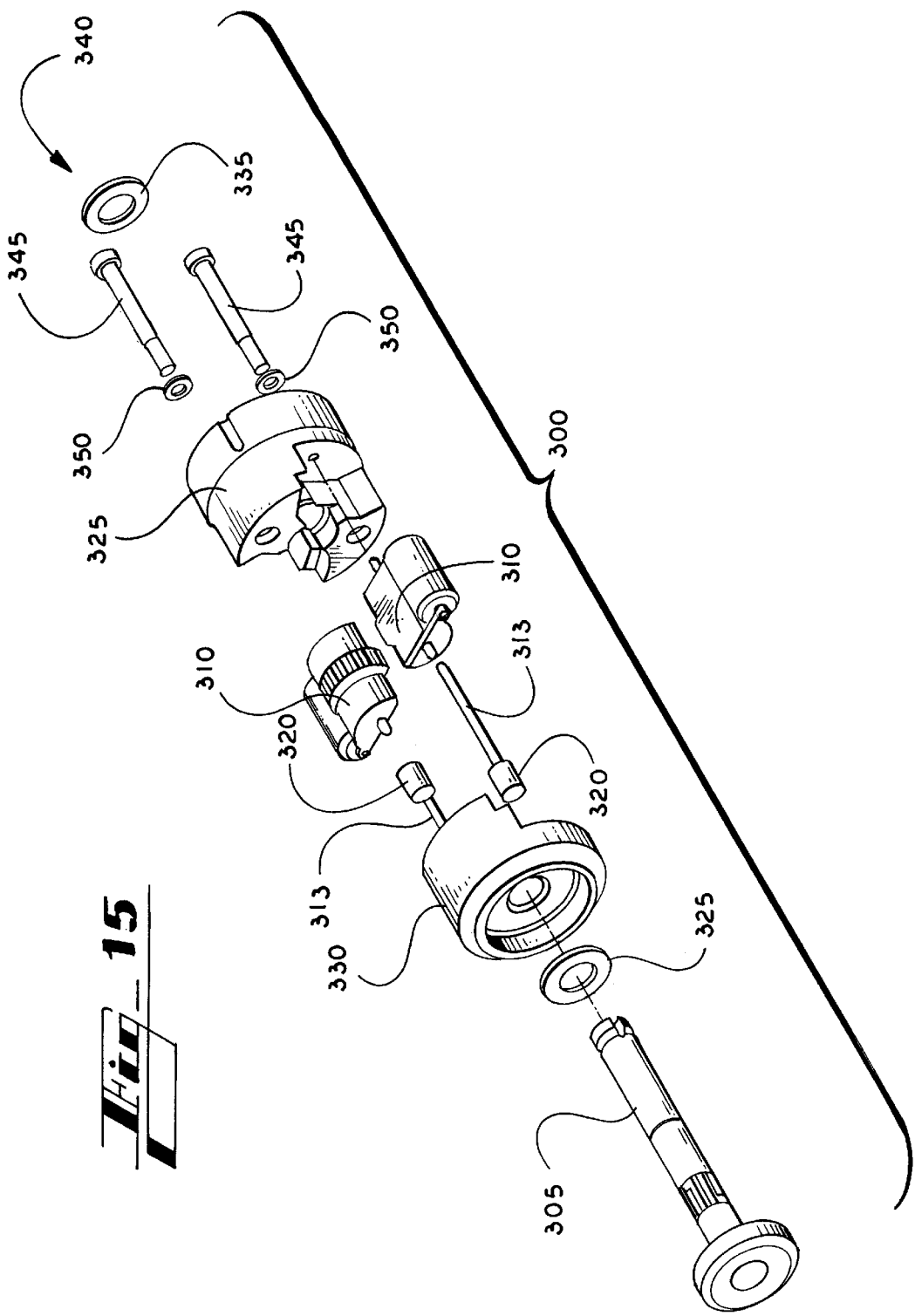

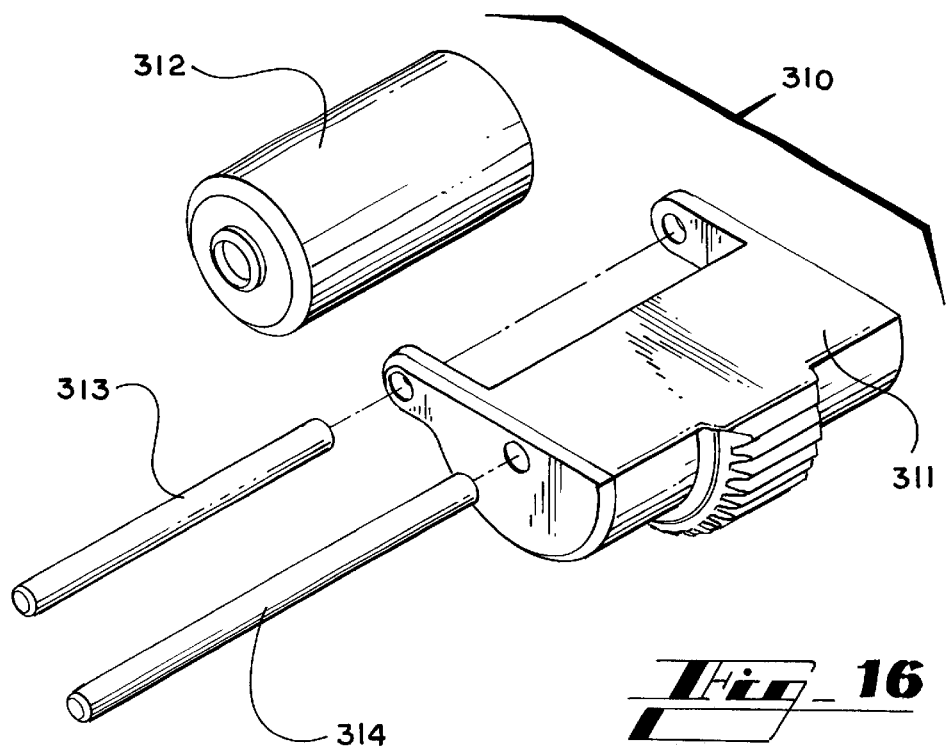
Fig_16
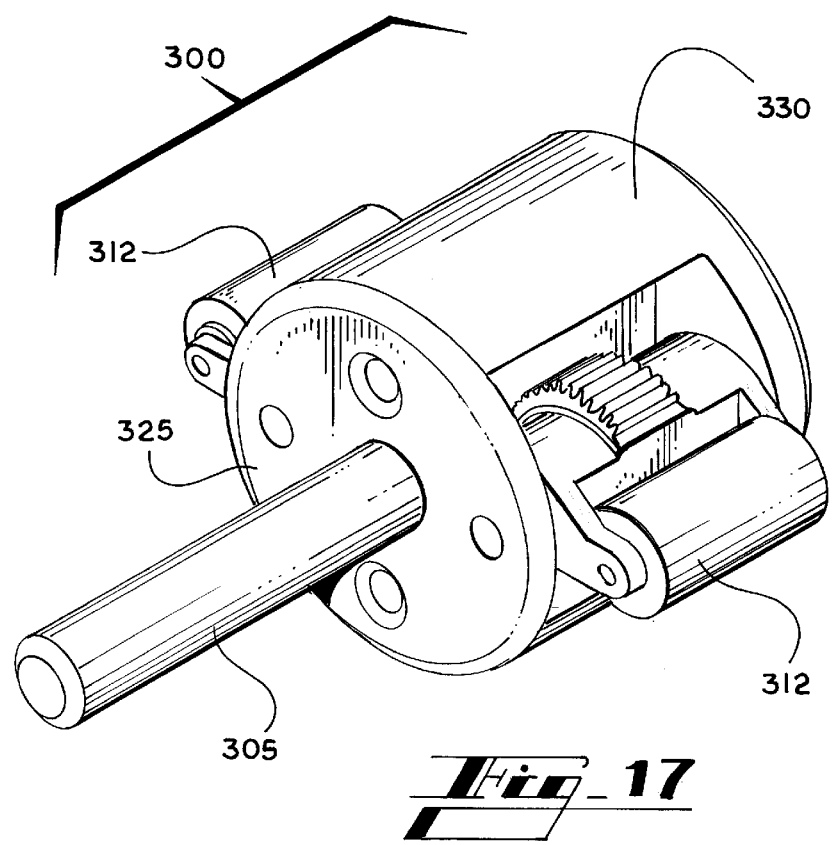
Fig_17

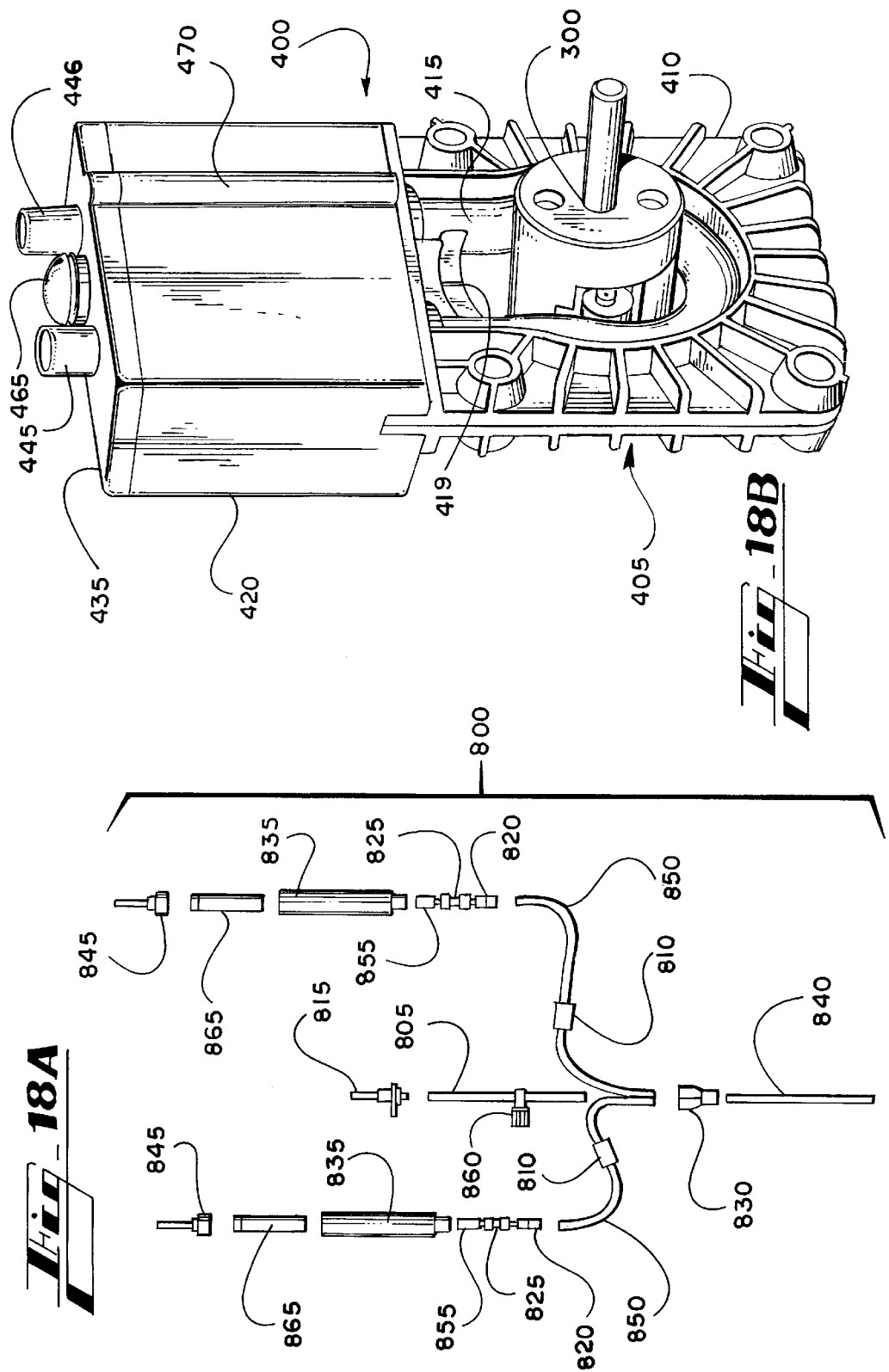

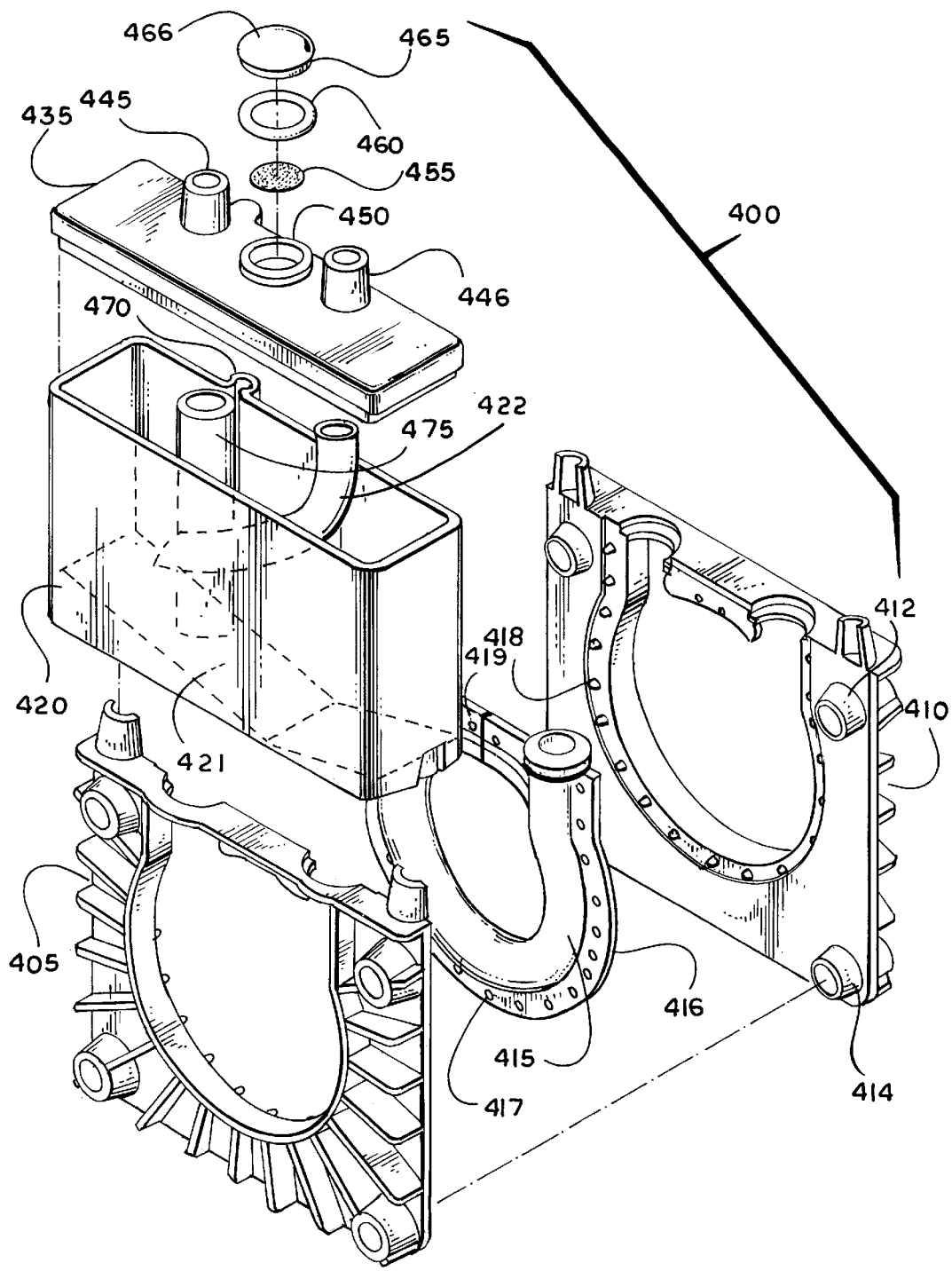
Fig_19

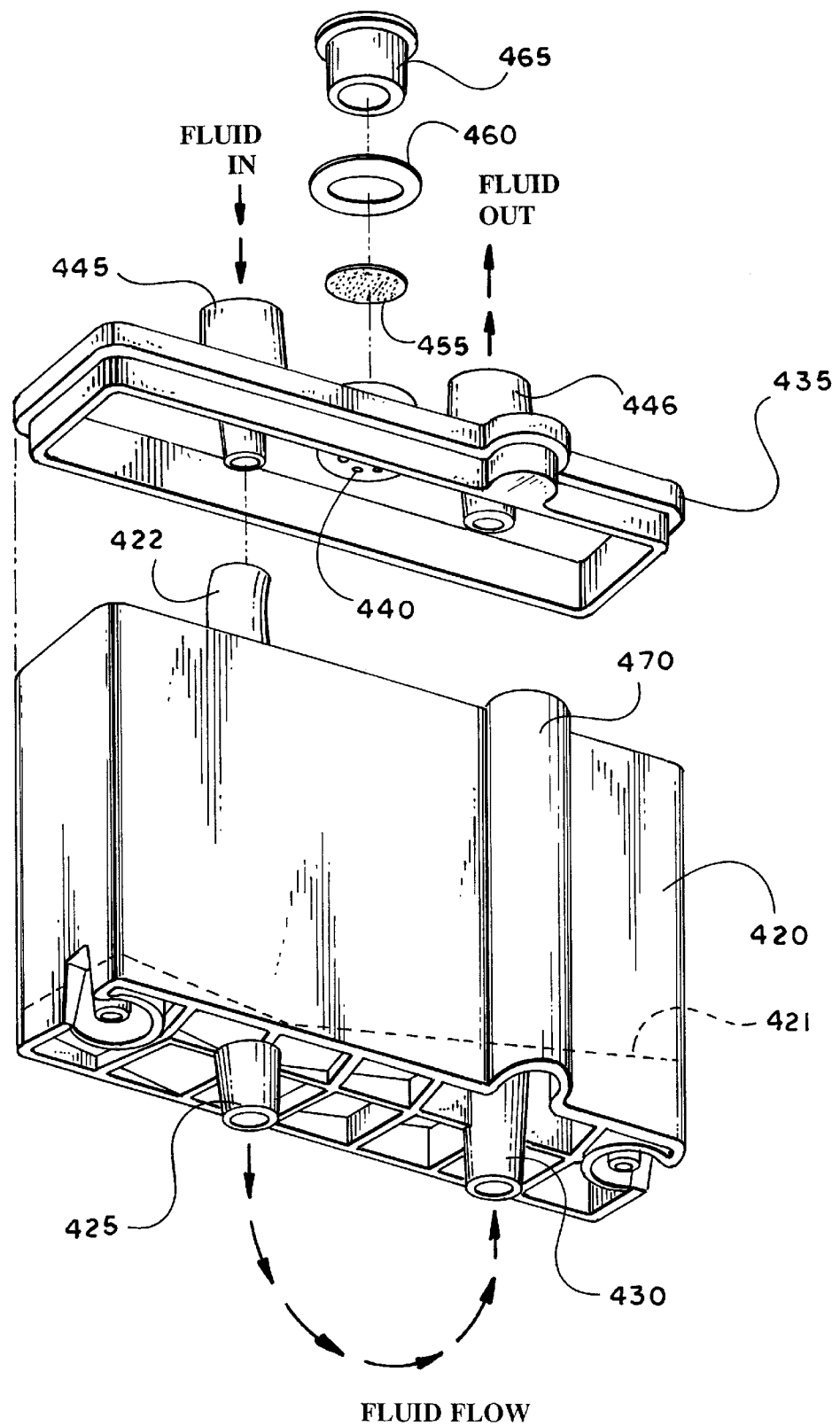

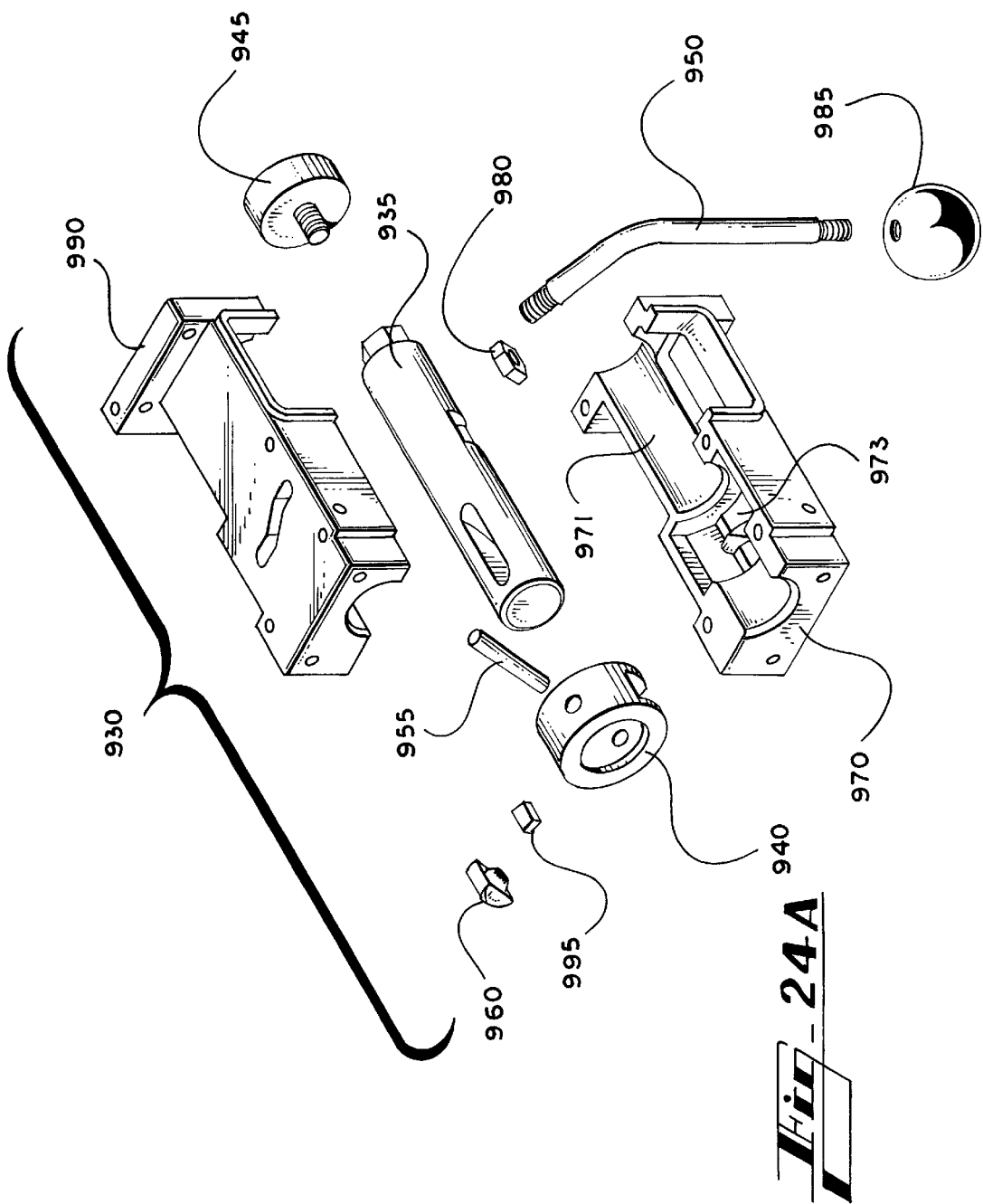

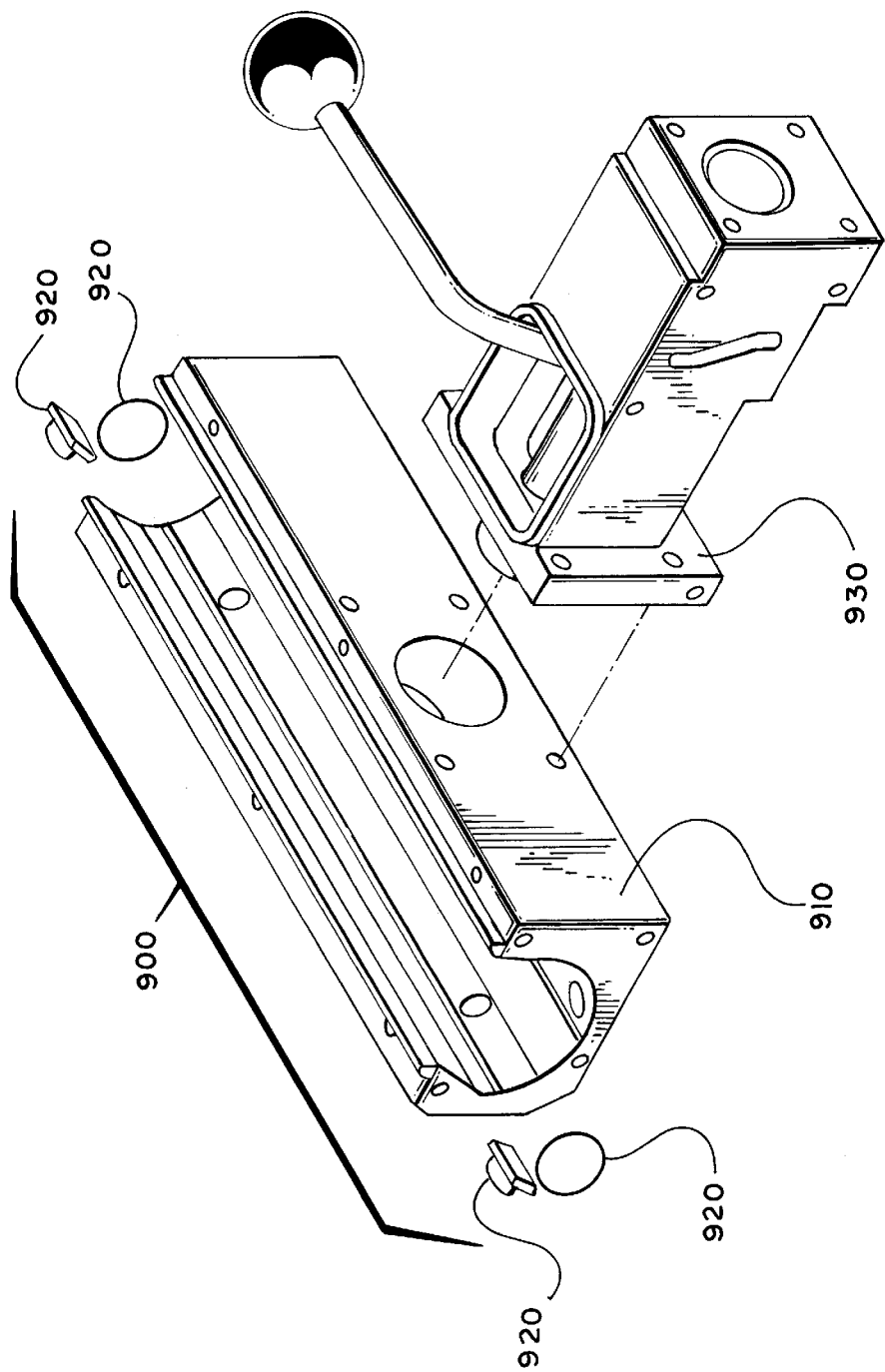

RAPID INFUSION SYSTEM

RELATED APPLICATION

This application claims priority to U.S. Ser. No. 60/156,674, filed on Sep. 29, 1999.

FIELD OF THE INVENTION

The invention relates to medical devices and methods for the infusion of fluids such as blood, blood products, and medications into a patient requiring circulatory volume replacement, with a capability for infusion over a range from slow to extremely rapid flow rates.

BACKGROUND OF THE INVENTION

A variety of clinical circumstances, including massive trauma, major surgical procedures, massive burns, and certain disease states such as pancreatitis and diabetic ketoacidosis can produce profound circulatory volume depletion, either from actual blood loss or from internal fluid imbalance. In these clinical settings, it is frequently necessary to infuse blood or other fluids rapidly into a patient to avert serious consequences.

In the past, the replacement of large amounts of fluids has been a major problem to the medical or surgical teams attending a patient with these acute needs. A common method of rapid infusion involves the simultaneous use of a plurality of infusion sites. Frequently, a plurality of medical personnel are required to establish and oversee the various infusion sites and to personally ensure the flow of fluids from their respective container bags. This method may be limited by the number of peripheral or central sites that can be physically accessed in a given patient, the number of people attending the fluids being infused, as well as the efficiency of infusing the fluids during a dire, hypovolemic event. It is not uncommon for four to five anesthesiologists or technicians to stand in attendance during transplant operations lasting more than twenty-four hours attempting to infuse massive quantities of blood through five or six venous catheters.

Patients who have undergone massive trauma or surgery such as liver transplantations or other elective procedures may require voluminous quantities of fluids to maintain a viable circulatory state. Although it is not uncommon for an anesthesiologist or surgeon in a major trauma and transplantation center to encounter massive exsanguination of ten liters or more, it is unusual to successfully resuscitate a patient with such massive blood volume loss using traditional methods.

While the potential need for rapid infusion is present in a number of common clinical situations, the actual need is unpredictable and may arise suddenly during the course of treatment or surgery. Therefore, it would be advantageous to have a system that could rapidly transition from normal infusion to rapid infusion with minimal operational intervention.

In patients suffering blood loss, measuring the pressure in the large central veins (central venous pressure or C.V.P.), is a good objective method for assessing the efficacy of volume replacement. A low C.V.P. indicates that the patient does not have adequate intravascular volume and thus further fluid resuscitation is necessary. A high C.V.P. is an indication of volume overload and can result in heart failure and pulmonary edema (or fluid) in the lungs. Presently, C.V.P. is most commonly measured by placement of a large catheter in the patient's neck that is connected to a pressure transducer. This transducer converts pressure changes into an electrical signal that is displayed on an oscilloscope-type monitor. Intensive care units and operating rooms are usually the only hospital areas capable of measuring C.V.P. In an emergency department setting, fluid administration is gauged empirically using mainly the patient's blood pressure and pulse to assess the adequacy of volume replacement.

Rapid infusion devices are best used while monitoring C.V.P. The volume and rate of flow into the patient can then be quickly and accurately adjusted to sustain an adequate C.V.P., lessening the chances of complications of heart failure and pulmonary edema from fluid overload.

The prior art contains a number of devices and methods that have attempted to address the clinical need for rapid intravenous fluid infusion.

U.S. Pat. No. 5,840,068 to Cartledge discloses a device and method for the rapid delivery of an infusion of blood and/or volume expanding fluid to a patient. The device includes a pump system that interfaces with a fluid housing system.

U.S. Pat. No. 5,061,241 to Stephens, et al. discloses a rapid infusion device capable of high volume pumping. The device includes a permanent unit that includes a base portion that houses an AC/DC motor, a roller pump, and other associated gauges and switches. A disposable unit includes a fluid housing, heat exchange component, and associated tubing leading to the roller pump. The roller pump increases the volume of fluid being pumped by increasing the r.p.m. of the pumping unit and includes a pressure control valve.

U.S. Pat. No. 4,747,826 to Sassano discloses a portable infusion system consisting of supply sources, fluid housings, and associated tubes and valves leading to an infusion pump which can be a centrifugal or a roller head occlusive pump.

U.S. Pat. Nos. 4,187,057 and 4,537,561 to Xanthopoulos disclose peristaltic infusion pumps employing disposable cassettes to house the infused fluid. In the '057 patent, the fluid conduit is held in the cassette in an arcuate configuration for its active interface with a pump rotor assembly. In the '561 patent, the fluid conduit is held in the cassette in a linear configuration for its active interface with a pump rotor assembly. It appears that the pumps can provide only routine infusion rates.

U.S. Pat. No. 4,410,322, to Archibald discloses an intravenous infusion pump that employs a piston-cylinder pump and a disposable pump chamber. The pump chamber contains a linear series of diaphragm enclosures that propel the infused fluid from the action of the pump cycles. Dielectrical sensors are employed to detect the presence of air bubbles in the disposable pump chamber. When air is detected by the system, an alarm is sounded for operator intervention.

Intravenous infusion rates may be defined as either routine, generally up to 999 cubic centimeters per hour (cc/hr), or rapid, generally between about 999 cc/hr and 90,000 cc/hr (1.5 liters per minute) or higher. Most prior art infusion pumps are designed for medication delivery and are limited in their performance to the routine range of infusion rates. Such pumps are not capable of rapid intravenous infusion. Although some prior art infusion systems can deliver rapid infusion, those prior art rapid infusion devices are physically large, complex systems that require dedicated operation by skilled technicians.

Accordingly, what is needed is a device for rapid infusion that is compact and easily operated by conventional medical personnel in the course of their other duties. What is also needed is a low to high speed infusion device that utilizes a sterile, disposable fluid containment system that can be readily attached and removed from a separate pump system.

SUMMARY OF THE INVENTION

The rapid infusion system described herein is an adjustable mechanical pumping system for the intravenous delivery of fluids such as, but not limited to, blood, blood products, physiologic fluids, and medications. The present invention has several novel features that distinguish the rapid infusion system from the prior art. The present invention is much safer than prior art devices in that the present invention includes a self-leveling drip chamber that decreases the possibility of air entering the system thereby protecting the patient from air embolism. In addition, the self-leveling drip chamber adds to the efficiency and ease of use because the operator will not have to shut the system down to purge air from the lines.

Another advantage of the present invention is an integrated motor drive that allows the device to deliver a wide range of flow rates of fluids from a unit that is small and compact. In addition, the present invention provides a wide variety of flow rates with no change in the configuration of the drive system. Another advantage of the present invention is the pump chamber and drip chamber are in one disposable unit that is easily installed by the operator of the device. All of these unique features provide a rapid infusion system that is (1) small, light-weight and relatively inexpensive because of the simple design of the device; (2) flexible because the device can deliver wide ranges of flow rates of fluids without the need to change the configuration of the drive system; (3) safe because the possibility of air entering the delivery tubing is virtually eliminated; and (4) easy to use because the pump chamber and the drip chamber are in one, easily installed unit. The present invention is capable of rapidly delivering fluids with greatly reduced operational demands to a patient suffering from acute hypovolemia. The rapid infusion system offers improved mechanical functions and desirable operational improvements over previously known systems and practices in the management of critical, life-threatening situations.

In one preferred embodiment, the rapid infusion system includes a pump assembly, a drive assembly to power the pump, and a fluid containment system that keeps the infused fluid out of direct contact with the pump assembly and that is preferably disposable and removable. The system optionally includes components such as a pressure sensor and controller, a temperature sensor and controller, a filter to remove any occlusive material from the fluid, an automatic self-leveling system to keep the fluid in the drip chamber at an appropriate level for maximal delivery efficiency, and a sensor system to detect the presence of air bubbles in the fluid in conjunction with a switch that can stop the flow in the conduit in response to a detected air bubble of a dangerous size.

The flow rate of the pump advantageously is continuously adjustable and, preferably, can provide fluid flow rates from less than 20 cc/hour to more than 1,500 cc/minute. In a preferred embodiment, the pump is a roller pump and is connected with a drive assembly using a differential assembly to provide seamless transition from standard flow rates to high flow rates.

The present system provides a cost effective, yet safe method of handling sterile infusions, as all components of the system that physically contact the infused fluid are contained within or attached to a sterile, disposable cartridge designed for single use. In one embodiment, the single use pump cartridge includes a section of pre-formed tubing serving as the pump chamber. The cartridge includes a drip chamber that is self-leveling. Optionally, the system may include a temperature sensor at the output of the temperature controller for measuring and adjusting the fluid temperature to maintain the temperature within acceptable limits. Other embodiments of the system may also incorporate other monitoring sensors and feedback devices to allow adjustments to be made by the infusion system in response to physiologic measurements, such as central venous pressure, pulmonary arterial wedge pressure, urine output, pulse, mean arterial blood pressure, and similar parameters. Still other embodiments of the system may incorporate other monitoring sensors and feedback devices to allow either quantitative or qualitative adjustments in the infusium in response to in vivo sensors measuring parameters such as arterial pH, serum potassium, serum glucose, and other physiologic or chemical factors. The system also preferably includes a user display, which displays parameters including fluid temperature, line pressure, fluid flow rate, and total volume of fluid infused.

A further advantage of this system is that it does not require dedicated technical personnel for its operation, and it can readily be programmed and operated by nursing or emergency personnel in the course of their other patient care duties. Yet another advantage of this system is an electronic control system that allows precise, in vivo monitoring of blood pressure and/or chemistries, and the system may be programmed to make precise and automatic adjustments of the infusion rate to the patient based upon the monitored parameters.

An object of the present invention is to provide an adjustable system that is capable of standard to high volume infusion of fluids into a patient requiring such treatment.

A further object of the present invention is to provide a single-use, disposable fluid containment system for an infusion system that interfaces with permanent pump and control systems to provide safe, sterile, and contamination-free delivery of fluids to a patient.

Another object of the invention is to provide a pump cartridge for an infusion system that is fluid self-leveling.

Still another object of the invention is to provide a rapid infusion system that can deliver fluid at normal and rapid rates, and that can smoothly transition between normal and rapid infusion rates. In one embodiment, this smooth transition is achieved using a differential driver assembly that interacts with more than one motor and drives the pump.

BRIEF DESCRIPTION OF THE DRAWINGS

Referring to the drawings:

FIG. 1 is a front elevational view of one embodiment of the rapid infusion system showing the housing, the control panel, a heater cartridge, and the disposable infusion pump cartridge in their respective operational positions within the rapid infusion system.

FIG. 2 is a partially assembled view showing the interaction between the drive assembly and the pump roller head assembly in one embodiment of the rapid infusion system.

FIG. 3 is an exploded view of the drive assembly used in one embodiment of the rapid infusion system.

FIG. 4 is an exploded view of a differential box assembly used in one embodiment of the rapid infusion system.

FIG. 5 is a cross-sectional view of a differential box assembly used in one embodiment of the rapid infusion system.

FIG. 6 is an exploded view of a yoke assembly used in one embodiment of the rapid infusion system.

FIG. 7 is an exploded view of a gear shaft assembly used in one embodiment of the rapid infusion system.

FIG. 8 is an exploded view of a bearing plate assembly used in one embodiment of the rapid infusion system.

FIG. 9 is an exploded view of a worm bevel gear assembly used in one embodiment of the rapid infusion system.

FIG. 10 is an exploded view of a stepper gear assembly used in one embodiment of the rapid infusion system.

FIG. 11 is an exploded view of a stepper motor assembly used in one embodiment of the rapid infusion system.

FIG. 12 is an exploded view of a gear box assembly used in one embodiment of the rapid infusion system.

FIG. 13 is an exploded view of a high speed motor assembly used in one embodiment of the rapid infusion system.

FIG. 14 is an exploded view of a mount plate assembly used in one embodiment of the rapid infusion system.

FIG. 15 is an exploded view of a pump roller head assembly used in one embodiment of the rapid infusion system.

FIG. 16 is an exploded view of a pivot arm assembly used in one embodiment of the rapid infusion system.

FIG. 17 is a view of a partially assembled pump roller head assembly used in one embodiment of the rapid infusion system.

FIG. 18A is an exploded view of the IV infusion tubing system used in one embodiment of the rapid infusion system.

FIG. 18B is a perspective view showing the interaction between the pump head and the disposable infusion pump cartridge in one embodiment of the rapid infusion system.

FIG. 19 is an exploded view of one embodiment of the disposable infusion pump cartridge assembly.

FIG. 20 is another exploded view of one embodiment of the disposable infusion pump cartridge assembly, showing details from below the cartridge unit.

FIG. 24A is an exploded view of the components of the pole clamp assembly used in the exemplary embodiment of the rapid infusion system.

FIG. 24B is an assembled view of the pole clamp assembly used in one embodiment of the rapid infusion system.

DETAILED DESCRIPTION OF THE PREFERRED EMBODIMENTS

Figure 21:
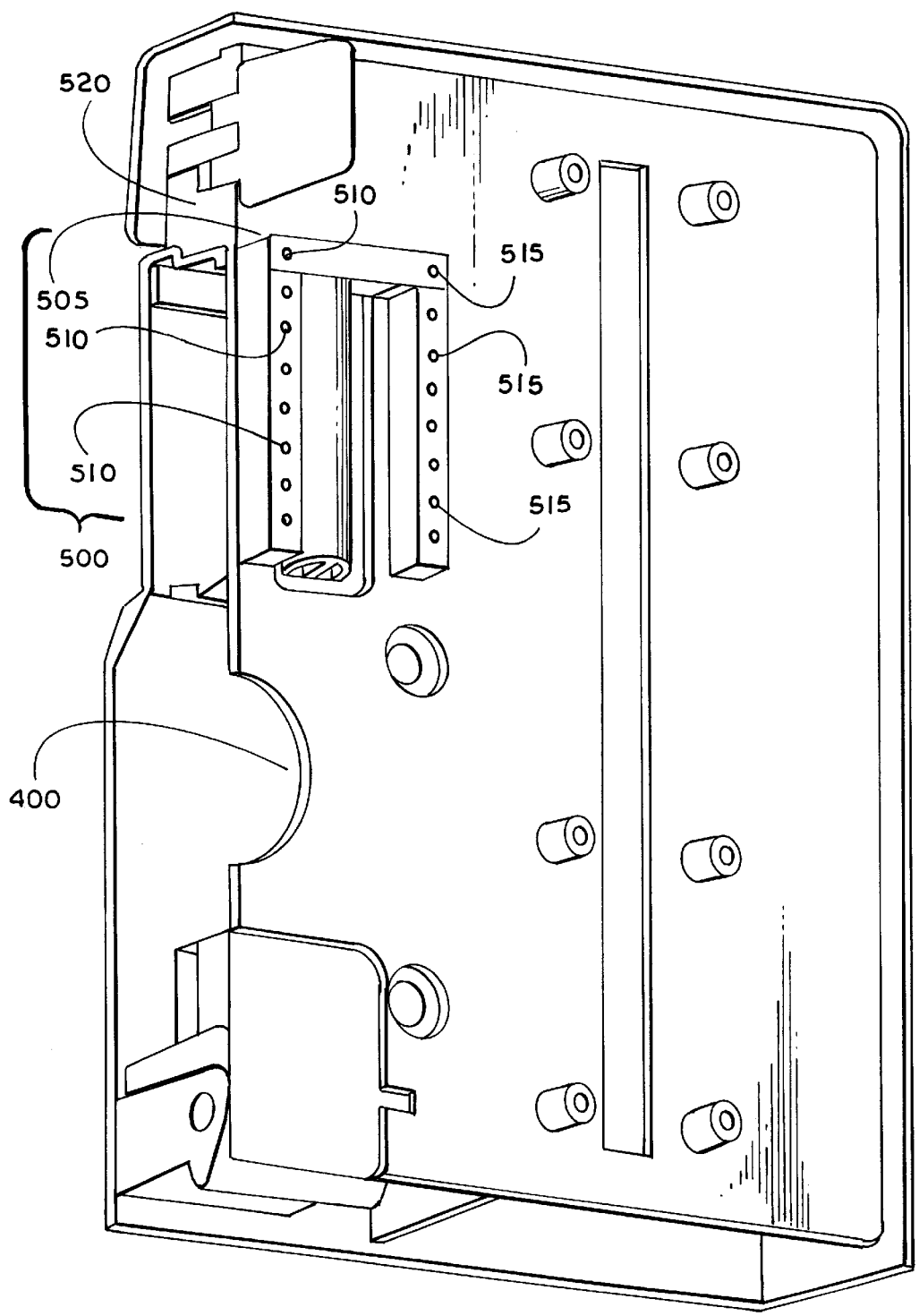
FIG. 21 illustrates the components of the automatic fluid self-leveling system in the exemplary system.

A system for rapid, intravenous infusion of a fluid is disclosed. The term "fluid" as used herein refers to blood, plasma, platelets, cryoprecipitates, blood products, physiologic fluids, medications, and other blood products and blood components. The system includes a drip chamber having an intake port for receiving the fluid and an outlet port for dispensing the fluid. The drip chamber is preferably included in a pump cartridge that may also include the pump chamber. A pump assembly propels the fluid through the system, and can include a gear pump, a turbine pump, a roller head occlusive pump, a nonocclusive centrifugal pump, or the like. The pump advantageously is adjustable and can provide fluid flow rates from less than 20 cc/hour to more than 1500 cc/minute.

The system further includes a drive assembly for driving the pump and one or more motors for powering the drive. Optionally, the system can include a fluid temperature controller, one or more optional filters to remove occlusive materials from the fluid, optional fluid pressure sensors, temperature and bubble sensors, tubing, catheters, and other conduits for infusing the fluid into the venous system, and conduits for conveying the fluid to and from each of the components of the system. Additionally, the system can include an automatic self-leveling system to keep the fluid in the drip chamber at an appropriate level for maximal delivery efficiency. Another optional component is a sensor system to detect the presence of air in the fluid in conjunction with a switch that can stop the flow and optionally sound an alarm in the conduit in response to a detected air bubble of a dangerous size.

In a preferred embodiment, the rapid infusion system described herein is composed of two major portions. One such portion includes permanent equipment, i.e. equipment that does not physically contact the infused blood or fluid and-thus need not be sterilized. In one embodiment, the permanent components include the pump gears or rollers, the drive assembly, one or more pump motors and related controls, optional monitoring equipment such as a C.V.P. monitor and related controls, an optional heating element and related controls, and an attachment adapter. The other portion includes optionally removable, disposable components such as the fluid containment system including a drip chamber, pump chamber, tubing, optionally a fluid heater cartridge and multiple conduits to access one or more IV bags or reservoirs.

As used herein, the term "pump chamber" refers to the region in the fluid flow path where motion is imparted to the fluid. In some cases, motion is imparted to the fluid by the action of a pumping mechanism located outside the pump chamber. Accordingly, when the pump is a roller head occlusive pump, a peristaltic pump, or a diaphragm pump, for example, the pump chamber can be separated from the pumping mechanism and the pumping mechanism does not contact the fluid. Since the pumping mechanism does not contact the fluid, it can be a permanent or semi-permanent piece of the infusion system. Alternatively, it can be included in the disposable fluid containment system.

In other cases, when the pump is a gear pump, a turbine pump, or a nonocclusive centrifugal pump, the pumping mechanism is contained within the pump chamber and fluid does contact the pumping mechanism. In this case the pumping mechanism, at least those portions that contact the fluid, is generally included as part of the disposable fluid containment system.

In one embodiment, the pump chamber forms a portion of a disposable pump cartridge. The pumping mechanism may also be included in this disposable cartridge.

Optionally, the system may further include temperature sensors at the input and output of the temperature controller for measuring and adjusting the fluid temperature to maintain the temperature within acceptable limits. The system may also incorporate monitoring sensors or devices to allow measurements and possibly adjustments to be made by the infusion system. The system may also have a user readout display, which displays parameters including, but not limited to, fluid temperature, line pressure, fluid flow rate, total volume of fluid infused, and trouble alerts such as "air in line", "overtemperature", and "overpressure".

In a preferred embodiment, the rapid infusion system can be powered by either A.C. or D.C. current. If powered by D.C. current, standard batteries can be used, including rechargeable batteries.

The rapid infusion system described herein can optionally infuse fluids and measure C.V.P. through a single central venous catheter. The device not only infuses fluid and monitors C.V.P., but the device can optionally adjust the flow rate automatically to achieve a programmed level of C.V.P. The device not only insures the ideal infusion rate for any particular patient but also is an inexpensive alternative to large, expensive C.V.P. monitors and obviates the need to place a second venous catheter dedicated only to C.V.P. readings.

The present invention can include a dial to set the desired C.V.P., a screen that displays the actual C.V.P., and an assembly that stops the pump at preset time intervals in order to accurately measure the C.V.P. The operator need only select how often the pump should stop, read the C.V.P., and adjust the flow rate accordingly. The system can alternately include feedback mechanisms to read the C.V.P. and adjust the flow rate. A manual mode is provided to infuse at a simple fixed rate with a switch that will halt the pump and give the operator an instantaneous C.V.P. reading. A pressure controller may be optionally used which maintains the C.V.P. within a preset range. The adjustable pump responds to signals from the pressure controller and increases or decreases the fluid pressure and/or flow rate in response thereto. Similarly, the present device can incorporate other in vivo physiologic monitoring devices to allow automatic regulation of infused fluids or medications within pre-programmed parameters. Advantageously, the device has an alarm indicating when the IV fluid bag(s) are nearly empty.

The invention is illustrated by the Figures and the following description of a particular embodiment that is not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

The system includes a pump that is driven by a pump drive assembly. The pump is preferably a roller head occlusive pump. The rotating action of the pump roller head assembly imparts a directional, peristaltic motion to fluid that is contained within the pump chamber, which is preferably a section of collapsible tubing. The pump chamber is contained in an infusion pump cartridge which also includes a drip chamber. The system preferably includes a fluid self leveling system to keep the fluid in the infusion pump cartridge at an appropriate level for more efficient pumping action. Before the fluid leaves the infusion system and enters the patient, an optional heater module brings the pre-infused fluid to near body temperature. In one embodiment, an electronic control system may be included which serves to operate the system within certain parameters that may be programmed beforehand, and is also capable of monitoring some physiologic factors and making programmed changes in the infusion rate based upon those factors. A power supply provides the necessary power. The power source can be either AC or DC. The infusion system can also be operated with power from an internal battery and includes a connection jack for attachment of an auxiliary battery. Finally, the system may employ an adapter for affixing the device onto a support stand while it is in use.

One embodiment of the infusion system is illustrated in FIG. 1, where the infusion system 100 includes a housing 115 with power cord storage brackets 120 to receive any excess A.C. power cord during use. The housing further encloses a pump drive assembly 200, a pump roller head assembly 300, a disposable infusion pump cartridge 400, an automatic self-leveling system 500, a heater module 600 containing a disposable heater cassette 610, an electronic control/display module 700, and a support attachment assembly 900. The housing may also include one or more handles to facilitate its transportation. Since the system is designed to be portable, it is desirable that it measure less than about 24 inches in any dimension and weigh less than about thirty pounds. However, it should be understood that while the relatively small size of the unit is advantageous, it is not critical to the invention.

FIG. 2 shows the relationship between the drive assembly 200 and the roller head assembly 300 in one embodiment of the present system. As described hereinafter, the roller head assembly 300 is attached to the drive shaft of the pump drive assembly 200. In this embodiment of the present invention, the roller head assembly 300 is semipermanently attached and can easily be removed for replacement or service.

FIG. 3 is an exploded view of the drive assembly 200 in one embodiment of the present system. The drive assembly 200 is the power core or drive train of this embodiment of the rapid infusion system 100. The drive assembly 200 includes a differential box assembly 205, a differential assembly 220, a stepper motor assembly 280, a gear box assembly 290, a gear box differential gasket 294, a high speed motor assembly 295, and a bracket assembly 299.

The differential assembly 220 allows the present invention to achieve a smooth transition between extremely high and low speeds. The differential assembly 220 provides for the attachment of a plurality of motors to a common drive output shaft. The high speed motor assembly 295 and the lower speed stepper motor assembly 280 are attached to the same output shaft 244 (see FIG. 2) by the differential assembly 220. The device can include other motor assemblies that attach to or interact with the drive shaft, such as an intermediate speed motor, for example. In an alternate embodiment, a smooth transition from slow to fast speed can be achieved using a larger stepper motor controlled by a controller.

The differential assembly 220 fits inside the differential box assembly 205 and is held in position by a snap ring 297. The gear box assembly 290 and the differential assembly 220 fit together with the gear box differential gasket 294 intervening between them. The stepper motor assembly 280 attaches to the differential box assembly 205 with a plurality of screws 296. The high speed motor assembly 295 attaches to the gearbox assembly 290 with a plurality of screws 298. The bracket assembly 299 is attached to the gearbox assembly 290 with a plurality of screws 287. The bracket assembly 299 affixes the drive assembly 200 to the inner surface of the base of the housing 115.

FIG. 4 is an exploded view that further details the assembly of the differential box assembly 205. The differential box assembly 205 includes a differential box 206, a bearing 207, a plurality of spacers 209, an RPM sensor 211, a spacer bracket 213, and a dowel pin 219. The differential box 206 houses the differential and provides a base to which other components are attached. The bearing 207 is received by a formed recess inside the wall of the gear box 291 (as shown in FIG. 12). The spacers 209 maintain proper alignment between the gearbox 291 and the differential box assembly 205, and between the attachment of the base of the differential assembly 220 to the inner surface of the housing 115. The spacer bracket 213 is mounted onto the differential box 206 by a plurality of machine screws 228. The RPM sensor 211 serves to track the rotations of the roller head assembly 300, and is attached to the spacer bracket 213 by one or more self tapping screws 217.

FIG. 5 is a cross sectional view detailing the differential assembly 220. The differential assembly 220 reduces wear on parts that would otherwise be produced by shifting gears. This serves to widen the range of speeds without a change in gear position. The differential assembly 220 includes a yoke assembly 222, a gear shaft assembly 240, a bearing plate assembly 250, a worm bevel gear assembly 258, one or more spider gear assemblies 264, a bevel gear 266, one or more curve washers 272, one or more Belleville washers 274, and a clutch bearing 276.

The yoke assembly 222 receives attachments from most of the components of the differential assembly 220 either directly or through the gear shaft assembly 240 that defines a central axis of the differential assembly 220. The bearing plate assembly 250 encloses the yoke assembly 222 within the differential box 206, as shown in FIG. 4.

FIG. 6 is an exploded view detailing the components of the yoke assembly 222. The yoke assembly 222 is the output shaft and the outer structure of the differential assembly. The yoke assembly 222 includes a bearing 226, a yoke 224, one or more pin shafts 230, one or more spring plungers 232, and a roll-pin 234. The bearing 226 is received into a slot in the yoke 224 and acts as the pilot bearing for the gear drive shaft assembly 240 (not shown). A plurality of machine screws 228 are positioned around the perimeter of the yoke 224. The machine screws 228 create magnetic spots that disturb the magnetic field, allowing the RPM sensor 211 (FIG. 4) to determine the rate of rotation of the shaft. The pin shafts 230 are received into bores in the fingers of the yoke 224 and act as shafts for the spider gear assemblies 264 (not shown). The spring plungers 232 are received into detent grooves in the roller head drive shaft 305 (not shown) on the roller head assembly 300 (not shown) and hold the roller head drive shaft 305 (not shown) in place. The roll pin 234 protrudes through the central axis of the output drive and interlocks with the roller head drive shaft 305 (not shown).

The gear shaft assembly 240 is further detailed in FIG. 7. The gear shaft assembly 240 includes a high speed drive shaft 244, and a high speed worm gear 248. The worm gear 248 engages the worm on the high speed motor 295 (not shown).

The bearing plate assembly 250 is further detailed in FIG. 8. The bearing plate assembly 250 supports the gear shaft assembly 240 (FIG. 5) to prevent flexing. The bearing plate assembly 250 also encloses the differential box 206, as shown in FIG. 3. The bearing plate assembly 250 includes a bearing plate 252, a bearing 254, and a clutch bearing 256. The clutch bearing 256 allows movement of the high speed drive shaft 244 in only a single direction. The bearing plate assembly 250 also supports the bearing 254 that encircles and supports the gear shaft assembly 240 (as shown in FIG. 5).

The worm bevel gear assembly 258 is further detailed in FIG. 9. The worm bevel gear assembly 258 transfers power from the low speed stepper motor 282 to the differential assembly 220. The worm bevel gear assembly 258 includes a worm bevel gear 260 and a bushing bearing 262. The worm part 260a of the worm bevel gear 260 engages the worm on the low speed stepper motor 295 (not shown), and the bevel part 260b of the worm bevel gear is one of the four gears that make up the differential assembly 220 (not shown). The bearing 262 presses into the center of the worm bevel gear 260 and allows the worm bevel gear 260 to spin freely around the gear shaft assembly 240 (not shown).

A spider gear assembly 264 is further detailed in FIG. 10. The spider gear assemblies 264 are two of the four gears that make up the differential. The spider gear assemblies ride freely on the gear shaft assembly 240 and transfer the force from the motors to the output shaft. Each spider gear assembly 264 includes a bevel gear 266 and a flanged bearing 268.

The stepper motor assembly 280 is the low speed drive, and its components are detailed in FIG. 11. The stepper motor assembly 280 includes a stepper motor 282, a worm gear 284, a shaft extension 286, and a bearing 288. The shaft extension 286 attaches to the output shaft of the stepper motor 282 with one or more set screws 289. The worm gear 284 attaches to the shaft extension 286 with one or more set screws 289. The stepper motor assembly 280 attaches to the differential box 206 as shown in FIG. 3, and the worm gear 284 engages the worm gear 260 on the worm bevel gear assembly 258 of the differential (not shown). The worm gear 284 eliminates the possibility of back driving, which could result in a loss of power. The stepper motor assembly 280 operates in a cycle of pulses, turning one step after each pulse.

Referring to FIG. 12, the gear box assembly 290 encloses and supports the gear shaft assembly 240 (not shown). The gear box assembly 290 includes a gear box 291, one or more dowel pins 292, and one or more bearings 293. The high-speed motor assembly 295 attaches to the side of the gear box assembly 290 as shown in FIG.3, and the dowel pins 292 further align the high-speed motor assembly 295. The bearing 293 contacts the high speed worm 248 and further supports the gear shaft assembly 240 (not shown).

The high-speed motor assembly 295 is the high speed power source and is further detailed in an exploded drawing in FIG. 13. The high-speed motor assembly 295 includes a high speed motor 302, a motor mount flange 304, a high speed worm gear 248, a high speed shaft extension 244, and a bearing 226. The high speed motor 302 is attached to the motor mount flange 304 by a plurality of machine screws 298. The high speed worm gear 248 is attached to the high speed shaft extension 244 by one or more set screws 289. The high speed shaft extension 244 is attached to the output shaft of the high speed motor 302 by one or more set screws 289. The high speed worm gear 248 engages the worm gear 260 on the gear shaft assembly 240 (not shown). The motor mount flange 304 provides a means for attaching the high speed motor 302 to the gear box assembly 290.

When the stepper motor assembly 280 is running, the clutch bearing 256 forces the bevel gear 266 to become stationary. When the high speed motor assembly 295 is running, the stepper motor assembly 280 forces the worm bevel gear 260 to become stationary, and the bevel gear 266 and the gear shaft assembly 240 to rotate. The yoke assembly 222 rotates around whichever gear is stationary at a given time, which is, in turn, determined by which of the motors is running at that time.

The mount plate assembly 235, as shown in FIG. 14 is the externally visible part of the pump drive assembly 200 to which the disposable infusion pump cartridge assembly 400 attaches, as shown later. The mount plate assembly 235 includes a mounting plate 236, long mount pins 237, and short mount pins 238. The long mount pins 237, and short mount pins 238 engage channels molded into the rear face of the rear cartridge frame 410 to guide and secure the long mount pins 237, and short mount pins 238 in position for use.

The roller head assembly 300, as detailed in FIGS. 15 and 17, is the drive part of the pump assembly. The roller head assembly 300 includes a roller head drive shaft 305, pivot arm assemblies 310, spacers 320, a roller cover bottom 325, a roller cover top 330, Teflon washers 335, a snap ring 340, cap screws 345, and lock washers 350. The pivot arm assemblies 310 extend and retract the rollers on the roller head drive shaft 305. In one embodiment of the infusion system, the roller head drive shaft 305 can be designed so that it is removable for replacement or service. Optionally, the roller head assembly 300 may easily be removed from the pump assembly for cleaning or replaced altogether for easier service. The roller head assembly preferably includes two rollers set about 180° apart to maximize filling of the pump chamber during operation. However, the assembly can include more than two rollers.

As shown in FIG. 16, each pivot arm assembly 310 includes a pivot gear 311, a roller 312, a stop pin 313 and a pivot pin 314. The pivot arm assemblies 310 hold the rollers 312 that ultimately contact the pumping chamber (shown as soft pump tubing 415 in FIG. 19), and impart peristaltic pumping motion to the fluid within the pump tubing 415. The pivot gears 311 on the pivot arm assemblies 310 engage with the gear on the roller head drive shaft 305.

The roller head assembly 300 is received by the output shaft 244 of the yoke 220 in the pump drive assembly 200 (as shown in FIG. 2). As the roller head drive shaft 305 turns in one direction, the pivot arms 310 are forced to turn in the opposite direction on the pivot pin 314. This outward rotation of the pivot arms 310 is controlled by the stop pins 313. Thus, the pivot-gears 311 and the roller head drive shaft 305 rotate as a unit. As the roller head drive shaft 305 turns, the rollers 312 roll along the pump tubing 415 (see FIG. 19) with the compression action of the rollers 312 causing fluid to move through the pump tubing 415.

Once the rollers extend to compress the tubing at a predictable tension, rotational motion of the entire roller head assembly ensues. This in turn causes peristaltic compression of the pump tubing thus imparting motion to the contained fluid. Once the rollers 312 are extended, the rotary motion of the roller head assembly 300 compresses the pump tubing 415 with a consistent, predictable tension level on each revolution.

Assembled portions of the roller head assembly are further illustrated in FIG. 17. The relationship between the roller head assembly 300 and the disposable infusion pump cartridge 400 are shown in a posterior perspective in FIG. 18B.

Portions of the fluid containment system.are illustrated in FIGS. 18A through 20. The fluid containment system includes a drip chamber and a pump chamber that are preferably assembled together in a disposable pump cartridge. The fluid containment system further includes IV tubing that directs infusium from one or more fluid reservoir(s) to the drip chamber, and an output infusion line that directs infusium from the pump to the patient. The fluid containment system can further include a heater cartridge, as described below.

The IV tubing system used in one embodiment of the rapid infusion system 100 is shown in FIG. 18A. The IV line assembly 800 carries fluid from the fluid reservoir(s), such as standard IV fluid bags or blood containers (not shown), to the infusion pump cartridge 400. In a representative embodiment, the IV line assembly 800 includes a main tubing line 805, one or more pinch clamps 810, a main blood spike 815, one or more female Luer locks 820, one or more male Luer locks 825, a Y-connector 830, one or more in-line drip chambers 835, one or more auxiliary blood spikes 845, one or more auxiliary tubing lines 850, one or more sections of tubing 855, a flow control pinch valve 860, and a filter 865.

The main spike 815 is inserted into the primary fluid reservoir. When the main spike 815 is not inserted into the reservoir, the main blood spike 815 is covered with a spike cap (not pictured). The fluid then flows from the fluid reservoir into the main tubing line 805. A flow control pinch valve 860 on the main line 805 allows the operator to control the rate of flow in relation to the other lines. The main line 805 then connects into a Y-connector 830 that provides for two auxiliary lines 850. Each auxiliary line 850 has a pinch clamp 810 that can be opened or closed to keep fluid from flowing prematurely through the line. Luer locks 820, 825 connect each auxiliary line 850 to a section of tubing 855 which fastens to an in-line drip chamber 835. The in-line drip chamber 835 allows the operator to visually monitor the rate of flow. Inside each in-line drip chamber is a filter 860. The filters 860 prevent contamination and the.passage of clots or other material that may occur in stored fluid.

Directly above each in-line drip chamber 835 is an auxiliary blood spike 845 for spiking auxiliary fluid reservoirs. Spike caps (not pictured) cover the auxiliary spikes 845 when not in use. The Y-connector 830 connects the main tubing line 805 and the auxiliary tubing line(s) 850 with a common input tubing 840 which connects to the pump tubing inlet port 425 of the disposable infusion pump cartridge 400 (See FIG. 18B.)

The infusion pump cartridge 400 includes a drip chamber and receives fluid from an external fluid reservoir. The infusion pump cartridge 400 mounts on the front of the rapid infusion system 100, such that the infusion pump cartridge 400 can interact with the infusion pump assembly 200 (FIG. 18B) and the automatic self-leveling system 500 (discussed below). Other embodiments of cartridges can alternatively be used in the presently described system.

FIGS. 19 and 20 are exploded views that detail the components of one embodiment of the infusion pump cartridge 400. The cartridge includes a front cartridge frame 405, a rear cartridge frame 410, and a formed pump tubing 415 which serves as the pump chamber, with retention flange 416. The cartridge further includes a drip chamber 420, a pump tubing inlet port 425 (FIG. 20) receiving the intake end of the pump tubing 415, a pump tubing outlet port 430 (FIG. 20) receiving the outlet end of the pump tubing 415, a vent cap 465 containing a central punctate aperture 466, a vertical optical chamber 470, internal outlet tubing 475 and a drip chamber top 435.

As further shown in FIG. 19, the front cartridge frame 405 and the rear cartridge frame 410 contain a plurality of upper holes 412 and lower holes 414, which serve to fix the assembled cartridge 400 to the short mount pins 238 and the long mount pins 237, respectively on the mount plate assembly 235 during system operation.

The pump tubing 415 is preferably molded from silicone or a similar soft, pliant material. The pump tubing 415 can have a variety of shapes, such as circular, semicircular, "U", or "Ω" shaped curve, with the inner curve sized and shaped to maximize the pumping action from-contact with the roller head assembly 300 (see FIG. 18B). In the embodiment illustrated, the pump tubing 415 is "U" shaped, but contains a spacer 419 at the upper pole of the curved tubing channels that serves to form a complete, 360° contact surface to provide constant resistance when the roller head assembly 300 interfaces with the pump tubing 415. The pump chamber is preferably tightly attached to the frame to prevent movement or dysfunctional deformation of the pump chamber during pumping. In the embodiment illustrated, the outer curve of the pump tubing 415 contains a retention flange 416 (FIG. 19), which is tightly retained within the front cartridge frame 405 and the rear cartridge frame 410 when the disposable infusion pump cartridge is assembled. The retention flange further contains a plurality of holes 417 that are retained by a plurality of symmetrically arranged retention pins 418 on the cartridge frame. The pins can be in the rear cartridge frame 410 as shown and can be retained by a plurality of matching indents (not visible) in the front cartridge frame 405.

The remaining elements of the infusion pump cartridge 400 are preferably fabricated of rigid plastic, such as PVC or polystyrene, for example. The front cartridge frame 405 and the rear cartridge frame 410 are bonded together during assembly, along with the pump chamber, the drip chamber 420, and the drip chamber top 435. The drip chamber top 435 is received by and retained by a friction fit within the drip chamber 420 by an inner flange (FIG. 20).

As shown in FIG. 18B, the pump tubing 415 connects to a drip chamber 420 through a pump tubing inlet port 425, and a pump tubing outlet port 430. The drip chamber top 435 further includes an inlet port 445 and an outlet port 446. The inlet port 445 and outlet port 446 are integral extrusions from the upper surface of the drip, chamber top 435. The inlet port 445 on the drip chamber 420 receives the infusion fluid from external fluid reservoir through conventional or modified I.V. tubing, and allows passage of the infused fluid into the interior of the fluid well 420. The outlet port 446 connects to the output infusion line (not shown). This output line can transfer blood to the heater (as discussed below) or directly to the patient.

The fluid containment system, including IV tubing 800, infusion pump cartridge 400, and output infusion line 880 can be assembled and supplied as one unit. The heater cassette 610, as discussed below, can also be assembled in this unitary assembly. In this way, all of the fluid contacting elements can be preassembled and sterilized. Complications such as delay and contamination can thus be avoided.

The drip chamber 420 can have a volume of about 20 to over 500 cubic centimeters (cc). The drip chamber 420 (FIGS. 20–21) has a sloping floor 421 from the outlet port 430 to the inlet port 425 to facilitate fluid flow out of the drip chamber 420. The inlet port 445 on the drip chamber is preferably connected to a diversion tube 422 that curves to deliver the fluid to the surface of the upper portion of the sloping floor 421. The diversion of the incoming fluid through the diversion tube 422 reduces the formation of air bubbles in the fluid and the possibility of additional hemolysis from cellular trauma that might result from a free fall of the fluid into the drip chamber 421. The pump tubing inlet port 425 and pump tubing outlet port 430 are integral extrusions from the lower surface of the fluid well 420. The central lumen of the pump tubing inlet port 425 freely connects with the interior of the fluid well 420. The pump tubing outlet port 430 connects with a rigid internal outlet tubing 475 that connects vertically with the outlet port 446 in the drip chamber top 435.

To minimize inadvertent air trapping within the system, the inlet port 445 in the drip chamber top 435 is preferably vertically offset from the pump tubing inlet port 425. Fluid cannot, therefore, drop directly through the fluid in the drip chamber into the pump tubing in the course of operation. Alternatively, or in addition, a baffle can be placed above the pump tubing inlet port 425 to deflect the inlet stream away from the inlet port 425 so that air bubbles do not enter the inlet port 425.

The drip chamber top 435 further contains a plurality of conical perforations 440 with rounded edges in their smaller openings in the upper surface of drip chamber top 435, for purposes as described below. The conical perforations 440 serve to allow the egress of air from the drip chamber 420 during auto-leveling, yet reduce the likelihood of an ingress of fluid into the pump responsible for purging air. The conical perforations 440 are covered by a filter 455, preferably hydrophobic, to further prevent fluid from entering the air purge pump, an O-ring 460, and a vent cap 465 which secures by a friction fit over the formed ring 450 in the upper surface of the drip chamber top 435. The height of the formed ring 450 in the upper surface of the drip chamber top 435 may be altered to maximize the efficiency of the automatic self-leveling system.

The infusion system preferably includes an automatic fluid self-leveling system that is designed to keep the cartridge drip chamber at an appropriate fluid level to facilitate the overall pump operation. The self-leveling system also serves as an air removal system to reduce the possibility of air embolism from inadvertent ingress of air bubbles into the infused fluid. The self leveling system includes a fluid level sensor to determine the level of fluid in the drip chamber and a fluid level controller to automatically fill the drip chamber to the desired level.

An optical chamber 470 extends from the rear surface of the drip chamber 420. The optical chamber contains a central lumen that is contiguous with the lumen of the drip chamber 420. The optical chamber 470 is a molded extension of the fluid well 420 and is preferably fabricated with transparent walls of optical quality.

Figure 22:
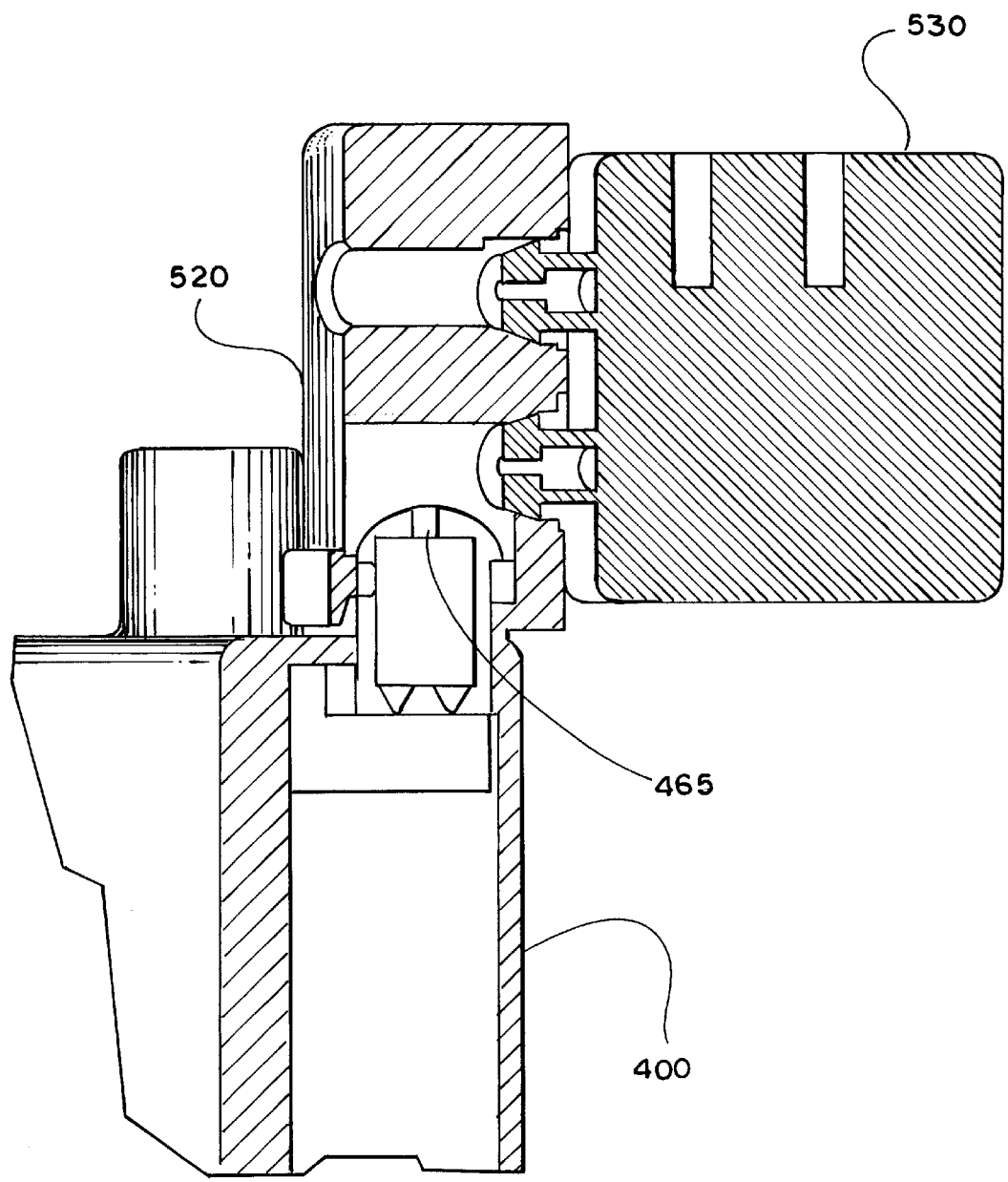
FIG. 22 details the interface between the drip chamber of the infusion pump cartridge and the diaphragm pump in the fluid self-leveling system in the exemplary embodiment of the system.

FIGS. 21 and 22 illustrates an automatic self-leveling system 500 and its relationship with the disposable infusion pump cartridge 400. As described above, the infusion pump cartridge 400 contains an integral optical chamber 470 that is continuous with the chamber. The optical chamber 470 is physically raised from the back surface of the drip chamber 420. When the disposable infusion pump cartridge 400 is inserted into the infusion pump assembly 100, the optical chamber 470 is aligned with a detector board 505 that is mounted vertically in a recess in the front of the housing 115. The detector board 505 is connected to a plurality of transmitters and detectors 515, preferably between five and ten, including sensors and transmitters 510. The sensors are preferably infrared sensors but can be other types of sensors, such as light or laser sensors or ultrasonic sensors.

A diaphragm pump 530 is mounted to the inner aspect of the housing 115 by a plurality of machine screws (not shown). Alternatively, the diaphragm pump can be placed at a distance from the housing with a connecting tube. The diaphragm pump 530 is an electrically powered diaphragm pump or any other pump that can exert a negative pressure. The diaphragm pump 530 contains a tubular interface 520 which connects to the intake port of the diaphragm pump 530. The diaphragm pump interface 520 further makes a friction fit over the vent cap 465 on the top of the infusion pump cartridge 400, when the cartridge is placed into its operational position within the rapid infusion system 100. The diaphragm pump 530 further includes a check valve (not illustrated) placed in an outlet line of the diaphragm pump 530 to reduce the possibility of air entering the drip chamber when the diaphragm pump 530 is inactive.

When the sensors 510 indicate that the fluid level within the optical chamber 470, and thus the drip chamber 420, has gone below a certain level, the diaphragm pump 530 is automatically activated and extracts air through the aperture in the vent cap 465 in the fluid well top 435 (FIG. 22). This creates a self leveling drip chamber to keep the fluid well 420 at an appropriate fluid level, with the resulting increase in pump efficiency. This has the effect of removing air that could be potentially embolic and detrimental to the patient's health. Desirably, the drip chamber stays at least 50% filled with infusion fluid, preferably at least 75% filled. The infusion system includes a shut off switch that will stop the pump if the fluid level in the drip chamber falls below a certain level, such as about 5% full, for example.

In another embodiment of the fluid level controller (not illustrated), a cap on the drip chamber can be opened automatically or by the operator to release air from the drip chamber. The pump is stopped to stop flow of fluid from the drip chamber. However, fluid continues to flow into the drip chamber from gravity and replaces air in the drip chamber until the fluid level is back to the desired range. The cap is then replaced and the pump resumed.

In another embodiment of the fluid level controller (not illustrated), the optical chamber 470 contains a small float that allows enhanced sensing of the fluid level by the sensors 510.

Figure 23:
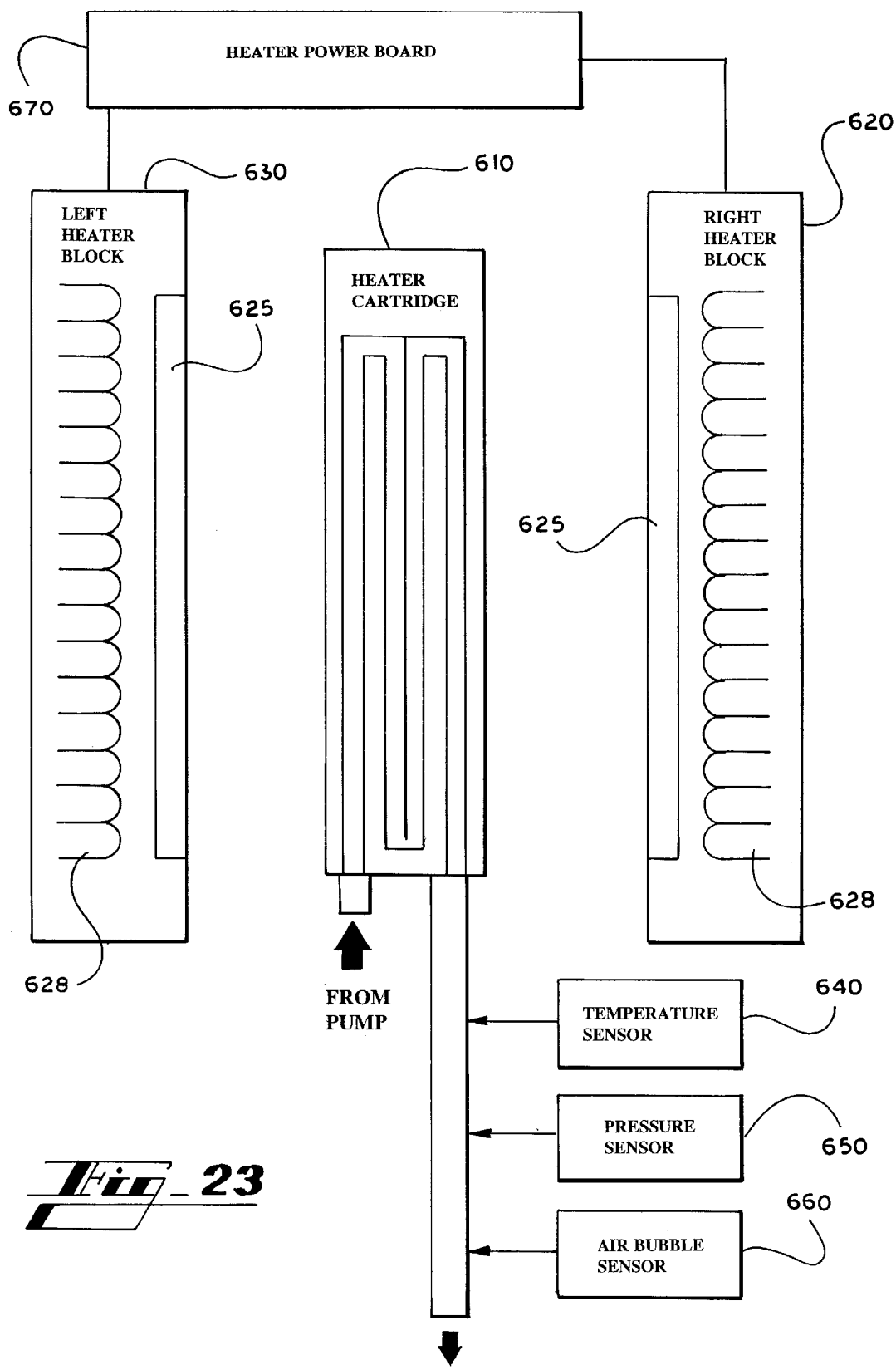
FIG. 23 details the heater module components and their relationships in the exemplary embodiment of the system.

When large volumes of fluid are to be infused into a patient, it is advantageous to heat the fluid to body temperatures before infusion to minimize any thermal insult during infusion. One embodiment of a heater module 600 is illustrated in FIG. 23. The heat module assembly 600 includes a right heater block 620, a left heater block 630, and a heater power board 670. Fluid from the pump flows from the pump cartridge 400 and into a separate, preferably disposable, heater cassette 610. The heater cassette can be modular and can be attached when needed. Entering at the bottom of the cassette 610, the fluid flows through a channeled internal pathway within the cassette 610 between the heater blocks 620, 630. The fluid is heated as it passes through the cartridge and the fluid exits through the distal end of the heater module 600. Having the fluid enter from the bottom and exit from the top further ensures that air is purged from the heater cassette. Each heater block includes a metallic plate 625 that covers an electric heating element 628. Fluid temperature and pressure within the heater module 600 are monitored by in-line thermal sensors 640 and pressure sensors 650. After the fluid finally exits the heater module 600, the fluid is monitored by sensors 660 to check for air bubbles before the fluid enters the patient through the output infusion line 880. Alternatively, the system can include an air bubble sensor in the outlet infusion line. Signals from the thermal sensors 640, pressure sensors 650, and air bubble sensors 660 are conveyed to the system's electronic control system for analysis and initiation of any necessary corrective or warning actions.

Alternative embodiments of the heater module 600 include use of a single heating element, use of three or more heating elements, use of a reflector to deliver additional heating function from the heating element(s), use of a linear or linear matrix fluid path instead of a channeled course, and/or use of a heated bath to provide the warming function. Energy sources that can warm fluids can include microwave or radiant heat sources.

A pole clamp assembly 900, shown in FIGS. 24A and 24B, and serves to attach the infusion system 100 or other system to an IV pole or similar vertical support member. The pole clamp assembly 900 works like a rifle bolt to clamp the infusion device or other system to a pole and securely lock it in place. The pole clamp assembly 900 accommodates a range of IV pole sizes from less than ½ inch to over 3 inches in diameter. One of the advantages of the pole clamp assemble is that, in one motion, the user can attach the device and lock it into place on poles of different diameters. The pole clamp assembly 900 includes an extrusion 910, a plurality of bumpers 920, and a pole clamp slide assembly 930.

The pole clamp slide assembly 930 further includes a shaft 935, a collar 940, a bumper 945, a handle, 950, a dowel pin 955, a wedge 960, a lower block 965, a hex nut 970, a knob 975, an upper block 980, and a spring 985. The pole clamp slide assembly 930 is the sliding piece that adjusts for and locks the infusion pump system to various sizes of IV or other support poles. The upper block 980 and lower block 965 contain a trough along their long axes that is sized to receive the shaft 935, thus holding the shaft 935 between the upper block 980 and lower block 965. The troughs of the upper block 980 and lower block 965 each provide a complimentary locking track, sized to receive the collar 940. The collar 940 goes over the shaft 935 and is guided into the locking tracks 990 by the dowel pin 955. The bumper 945 allows resilience at the end of the shaft and prevents marring of the support pole surface.

As the collar 940 rotates in the locking track 990, the wedge 960 is pushed inward and engages with the shaft 935. There are serrated teeth on the shaft 935 that engage teeth on the wedge 960. When the teeth lock, the entire pole clamp assembly 900 moves towards the pole. The spring 985 keeps the teeth on the wedge 960 from engaging in the process of making a gross adjustment. The extrusion 910 wraps around the IV pole, and the bumpers 945 provide a non-slip surface and prevent marring of the pole. Gross adjustments may be made by lifting the handle 950 up and sliding it forward. This action moves the pole clamp slide assembly 630 towards the pole. Turning the handle 950 downward locks the clamp into place.

Figure 25:
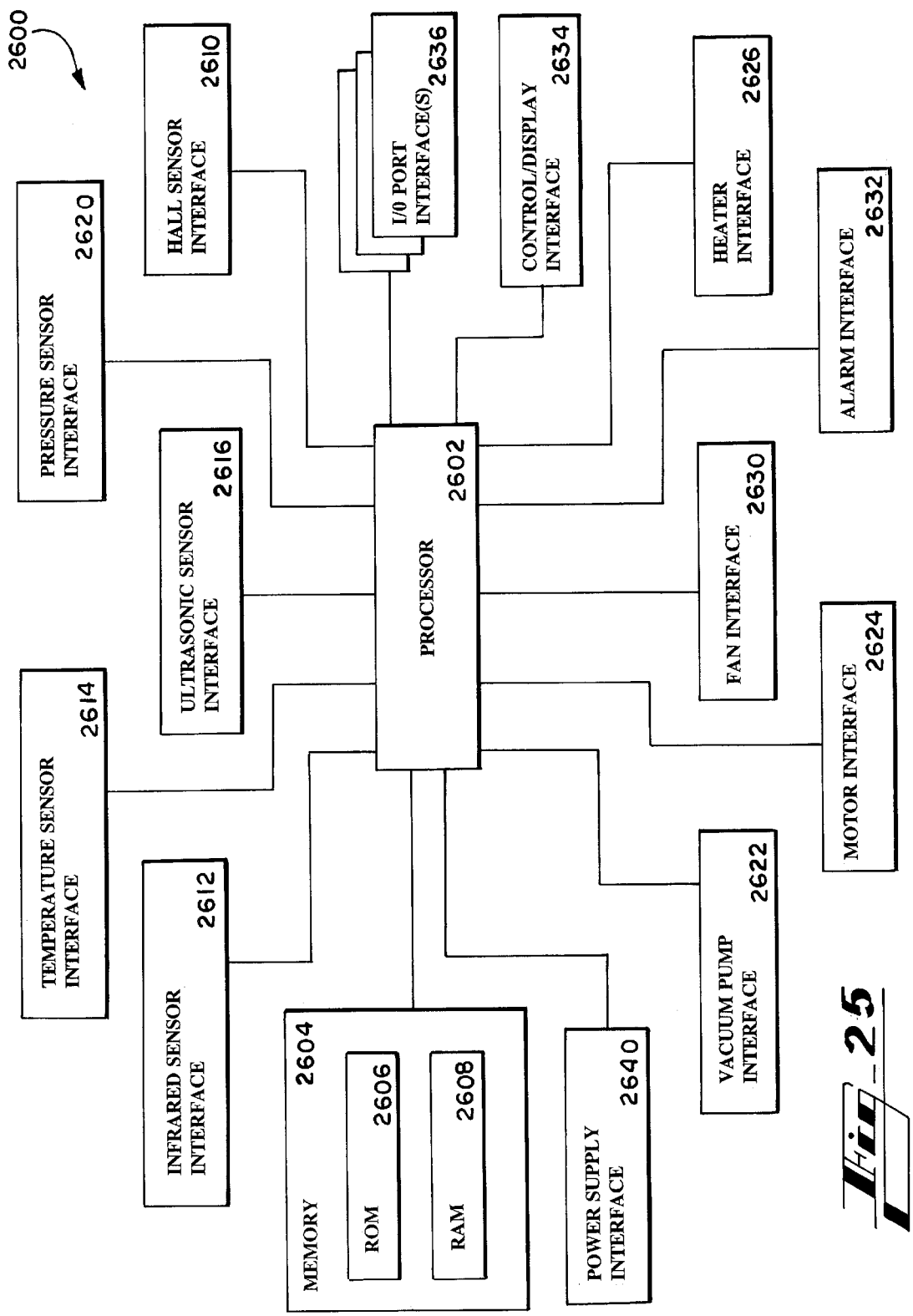
FIG. 25 is a block diagram illustrating the electronic control system of an exemplary embodiment of the rapid infusion system.

FIG. 25 is a block diagram illustrating an electronic control system 2600 of an exemplary embodiment of the present invention. The electronic control system 2600 employed in this embodiment serves to perform such functions as: regulating the pump drive assembly 200 and the heater module 600; monitoring and operating the automatic self-leveling system 500; communicating with physiologic monitoring devices and appropriately adjusting the pump function in response to physiologic factors; and communicating with medical personnel via user interface control/display panel 700. These and other functions of the present invention are controlled by the electronic control system 2600. It should be understood that the components forming the electronic-control system 2600 may be conventional components that are well known in the art.

A processor 2602 is provided for executing software and/or firmware stored in memory 2604, which controls the operation of the infusion pump system 100 of the present invention. By way of example, firmware may be stored in read only memory (ROM) 2606 and software may be stored in random access memory (RAM) 2608. Other types of memory storage devices may be provided, such as such as magnetic cassettes, flash memory cards, digital video disks (DVD), Bernoulli cartridges, EPROM, EEPROM, or any other type of computer-readable media. As is well known in the art, software is generally programmable and re-programmable. Therefore, via various user interfaces, the user may be provided with the ability to program and re-program the operating parameters of the infusion pump system 100.

The processor 2602 of the electronic control system 2600 communicates with the various sensors of the infusion pump system 100 by way of various corresponding interfaces. For example, an exemplary electronic control system 2600 may include a RPM sensor interface 2610 which facilitates communication between the processor and a RPM sensor 211 for monitoring the speed of the pump drive assembly 200. The exemplary electronic control system 2600 may also include an infrared sensor interface 2612, a temperature sensor interface 2614, an ultrasonic sensor interface 2616, and an air pressure sensor interface 2620 for facilitating communications between the processor 2602 and an infrared sensor 510, a temperature sensor 710, an ultrasonic sensor 725, and a pressure sensor 730 respectively. As mentioned previously, the temperature sensor and the pressure sensor may be used to monitor the temperature and the pressure, respectively, of the fluid as the fluid leaves the infusion pump system, while infrared sensor(s) and ultrasonic sensor (s) or other sensors may be used to detect air bubbles and other impurities.

The processor 2602 can transmit data to a remote location such as through a telephone or other data line. The processor 2602 can also receive data and instructions from a remote location.

The processor 2602 also communicates with the various electromechanical components of the infusion pump system 100 via various corresponding interfaces. By way of illustration, the electronic control system 2600 may include a diaphragm pump interface 2622, a motor interface 2624, a heater interface 2626, a fan interface 2630, and an alarm interface 2632. The electronic control system 2600 may also include a control/display interface 2634 for facilitating communication between the user control/display panel 700 and the processor 2602 and one or more I/O port interfaces 2636 for facilitating communication between the processor 2602 and various devices that may be received Via input/output ports. The electronic control system 2600 may further include a power supply interface 2640 for facilitating the supply of power to the processor 2602.

By communicating with the various sensors and the various electromechanical components of the infusion pump system 100 and by executing appropriately programmed software and/or firmware, the processor 2602 may be operable to automatically control the operation of the infusion pump system 100. For example, the processor 2602 may receive a user instruction from the control/display panel concerning a desired rate of fluid infusion. In response to the user instruction, the processor 2602 may interact with the RPM sensor interface 2610 in order to determine the rate of the pump drive assembly 200. In response to determining the rate of the pump drive assembly 200, the processor 2602 may interact with the motor interface 2624 in order to increase or decrease the speed of one or both of the stepper motor assembly 280 and the high speed motor assembly 295. The processor 2602 may also be operable to interact with the control/display interface 2634 in order to display the rate of the pump drive assembly 200 to the user on the control/display panel 700. The processor 2602 may be further operable to activate the fan 720 for the purpose of cooling the pump drive assembly 200, if the RPM sensor 211 indicates that the pump drive assembly 200 exceeds a particular rate.

As another example, the processor 2602 may be operable to maintain a given temperature for the fluid in the pump tubing 115 by interacting with the temperature sensor interface 2614 and the heater interface 2626. The given temperature may be a pre-determined default value or may be set by the user via the control/display panel 700 and communicated to the processor 2602 via the control/display interface 2634. In response to continuous temperature readings detected by the temperature sensor 710, the processor 2602 may be operable to adjust the heat output of the heater module 600 accordingly. Likewise, the processor 2602 may be operable to receive a signal from the infrared sensor interface 2612 or the ultrasonic sensor interface 2616 or other sensors indicating the presence of an air bubble or other impurity in the pump tubing 415. In response to an impurity signal, the processor 2602 may be operable to engage the diaphragm pump 530 for removing the impurity from the pump tubing 415. If an impurity signal persists, the processor 2602 may communicate with an alarm 705 via the alarm interface 2632 for generating a warning signal to the user. The processor 2602 may also be programmed to automatically power down the pump drive assembly 200 in response to undesired temperatures of the infusion fluid or persistent impurities in the pump tubing 415.

As a further example, the processor 2602 may be operable to communicate with other digitally-controlled machines or medical instruments via the I/O port interface(s) 2636 in order to receive patient measurements, such as the central venous pressure or other physiologic or chemical conditions of the patient. As such, any well known digitally-controlled machine or medical instrument may be integrated into, or operated in tandem with, the infusion pump system 100. The processor 2602 may be programmed to appropriately adjust the operation of the infusion pump system 100 in response to patient measurements.

All data signals received by the processor 2602 via a sensor interface, an I/O port interface 2636, or the control/display interface, may be translated into user readable symbols and displayed on the control/display panel 700 and/or may be stored in memory 2604. Accordingly, the processor 2602 may be programmed to retrieve data from memory 2604 and to perform calculations thereon. Such calculations may be specified by the user via the control/display panel 700 or may be predetermined default calculations. The processor 2602 may further be operable to display the results of such calculations on the control/display panel 700.

Figure 26:
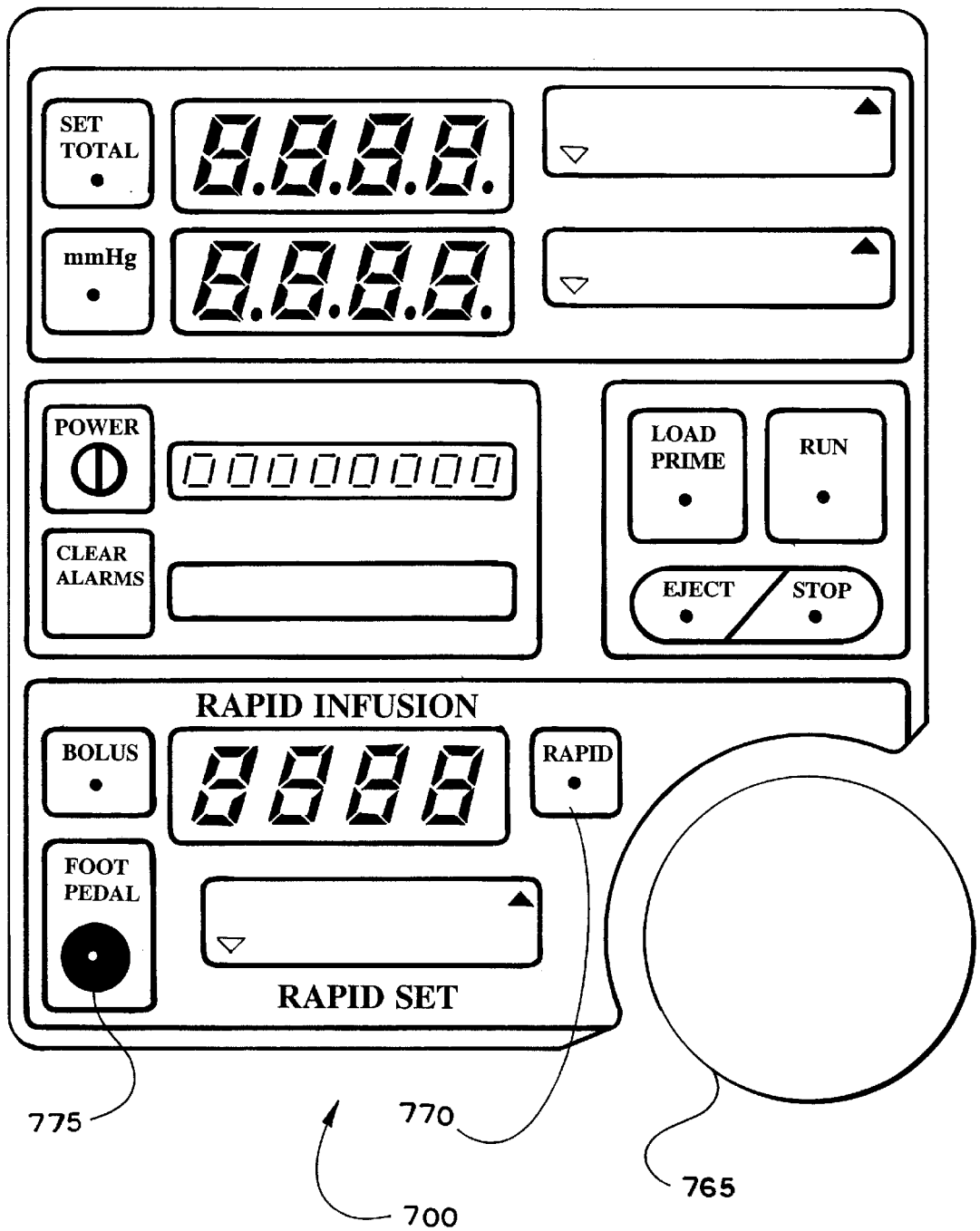
FIG. 26 details the electronic control/display user interface for an exemplary embodiment of the rapid infusion system.

FIG. 26 shows an electronic control/display user interface panel 700 in one exemplary embodiment of the rapid infusion system. In this example, the upper portion of the control/display array is for routine or standard infusion rates. The lower portion of the control/display array is for rapid infusion.

The rapid infusion system can optionally include a fluid rate titrator to allow the user to titrate from a standard rate to a rapid rate, in the event that rapid infusion is subsequently needed during treatment or surgery. In the illustrated embodiment the titrator is a voltage control circuit 765 used to regulate the voltage across the pump drive assembly 200. The user presets a rapid infusion rate. Activation of a single "Rapid" switch 770 unlocks a dial on the spring-loaded potentiometer and places the voltage control circuit 765 in series with the pump drive assembly 200. The user can then use the voltage control circuit 765 to vary the voltage applied to the pump assembly 200 to regulate the rate of increase of the flow rate. For example, the voltage control circuit can be a simple potentiometer, or variable resistor. When the user activates the "Rapid" switch, the potentiometer is enabled. The user regulates the voltage increase across the pump drive assembly 200 by adjusting the potentiometer dial. As the user increases the rotation of the potentiometer dial, the voltage across the pump drive assembly 200 increases. The increase in voltage is directly proportional to the degree of rotation of the dial. For example, if the standard infusion rate is set at 300 cc per hour and the rapid infusion rate is set at 1000 cc per minute, turning the potentiometer dial half way between the minimum and maximum positions would increase the infusion rate to 497.5 cc per minute.

The rate at which the voltage increases across the pump drive assembly 200 is directly proportional to how "fast" the user rotates the dial. Using the above example, if the user slowly turns the dial from the 300 cc setting to the 1000 cc setting, the rate at which the flow rate increases is also very slow. If, however, the user rotates the potentiometer dial very quickly, the infusion rate will increase from 300 cc per hour to 1000 cc per minute almost instantaneously. Therefore it is up to the user to manually regulate how fast the infusion rate increases from the normal setting to the final setting. Once the user releases the dial, the spring retracts and returns the potentiometer dial to its initial setting and the pump returns to the standard infusion rate.

In another example, the voltage control circuit 765 may be an infrared detector (IRD) coupled to a bank of light emitting diodes (LEDs). The output of the IRD is connected to the pump drive assembly 200. To apply a voltage to the pump drive assembly 200, the user activates at least one LED. The incident light upon the IRD creates a voltage at the output terminals of the IRD. To increase the output voltage, the user simply increases the amount of light incident upon the IRD. This may be accomplished by simply turning on additional LEDs.

To activate the LEDs, a spring-loaded dial may be placed in proximity to the leads of the LEDs. As the dial is rotated, it comes in contact with the leads of LEDs and forms a closed circuit causing the LEDs to light. As the dial is rotated farther, it contacts the leads of more LEDs, thereby increasing the amount of light falling on the IRD, and thus increasing the output voltage. However, each LED emits a discrete amount of light. Therefore, the increase in the output energy will in stepped up by discrete values. To remove these step variations, and ensure that the increase in flow rate is gradual, the output voltage may be passed through a low-pass filter before it is applied to the pump drive assembly 200.

Although the voltage control circuit 765 has been described in terms of a potentiometer and an IRD circuit, those skilled in the art will appreciate that other voltage control circuits may be substituted for those devices in the preferred embodiments without altering the scope of the invention.

A jack 775 on the display panel 700 offers a connection for an optional foot or hand control for the rapid infusion system. The optional foot or hand control would serve the same purpose as the potentiometer, with the added benefit of allowing the operator to work while moving around and, with the foot control, hands free.

Electrical power to the pump drive assembly 200, the automatic self-leveling system 500, the heater module 600, the electronic display system 700, the electronic control system 2600, and other parts is provided through the system power supply 2700 (not shown). The power supply 2700 derives its power either from external A.C. line current or from internal D.C. batteries. Standard circuitry is employed to connect the power source(s) through one or more standard transformers and then for delivery within the system. External batteries can also be used.

In addition, the power supply serves an electric cooling fan 720 of standard design, with the fan being mounted on or within the internal aspect of the system housing 115 (not shown). The cooling fan 720 is employed to reduce internal heat from the motors 280,295, heater module 600, diaphragm pump 530, and system electronics 2600. Operational switching and regulation of the fan 720 are optionally controlled by one or more thermal sensors 750 within the rapid infusion system 100.

OPERATION

The rapid infusion system can be operated as a low-speed infusion device for routine IV infusion. The infusion system can also be operated as a high-speed infusion device for rapid infusion of fluids to a trauma victim in an emergency room, at an accident scene, or in an ambulance, for example. The device can be particularly advantageous in situations where it may be preferable to first employ routine IV infusion followed by rapid infusion, followed again by routine infusion, such as during a transplant operation, for example. The device can be operated at rates ranging from less than 20 cc per hour to greater than 1.2 liters per minute and allows seamless transition of infusion rates.

The rapid infusion system is powered up by toggling a main power switch. If the unit is connected to a live AC power source, then the system will operate on AC power. If there is no AC power connection, or if AC power is interrupted, the system will automatically use its internal battery DC source. Residual battery power is monitored by the electronic control system during use, and user warnings are provided when battery strength is waning.

Conventional IV fluid or blood bags or bottles can be used, for example, or an alternate fluid reservoir can be employed, particularly when large quantities are to be infused. The bags or bottles are spiked with a delivery tubing that is connected to a disposable rapid infusion pump cartridge. The cartridge is inserted in the front of the infusion system, with the pump roller head in position in the center of the seated cartridge.

The holes in the cartridge frame then are placed over the corresponding posts on the mounting plate face, which hold the cartridge securely in position during pump operation. The load button is then activated to extend the rollers.

The user may program the system to deliver a set volume of infused fluid, at a selected infusion rate. Other control options include specifying certain target parameters such as C.V.P., when the system is equipped to monitor such functions.

If the user believes that rapid infusion might be needed, the user may preset a rapid infusion rate in the event there is a clinical need for this function. When the rapid infusion system is employed for routine IV infusion, the user has the option of pre-setting a rapid infusion rate in the event that a clinical need for this function arises. A spring potentiometer can be instantly triggered and activated by toggling a single "Rapid" switch if this operation is suddenly required. Activation of the potentiometer allows the.operator of the present invention to titrate the fluid rate to the patient from the routine rate up to a preset rapid rate.

Generic defaults for rapid rate and infusion volume settings are optionally programmed into the system, should a need arise before user selected values have been entered.

Additional controls allow for one button bolus administration, along with various monitoring functions. The system automatically monitors the fluid level in the drip chamber, and will engage a diaphragm pump to remove air if the fluid level gets too low. The system will automatically turn off the pump and alert the user if air bubbles are present in the outgoing tubing.

The heater module employs an additional disposable cartridge that is connected in-line with the infusion fluid to warm the fluid to body temperature before infusion into the patient. Additional electronic controls monitor both the temperature and pressure of the fluid as it exits the heater module.

When infusion has been accomplished, the disposable infusion pump cartridge may be removed from the device and discarded. The operator presses the "Load/ Unload" button, which causes the rollers in the pump head to retract, facilitating the cartridge removal, and protecting the roller mechanism.

If necessary for either cleaning or system maintenance, both the pump roller head unit and the roller head drive shaft may be readily removed and cleaned or replaced. All portions of the rapid infusion system that directly contact the infusion fluid are designed for sterile, single use and do not require cleaning.

Unlike standard or traditional methods of intravenous fluid administration, the rapid infusion system described herein can provide continuous total replacement of adult human blood volume through virtually any sort of hemorrhage, for an indefinite period of time and can rapidly regulate fluid temperature with minimal increase in resistance to flow, easily and rapidly administer massive quantities of blood to a single patient during a single operation, administer physiologic fluid maintained at a predetermined temperature at flow rates in excess of 1500 cc/minute, and permit simultaneous display and control of fluid temperature. The system can easily be carried and is able to be quickly and easily used in an emergency situation or by emergency personnel in the field. The blood delivered by the system can include clotting factors and can infuse an infinite amount of blood over an indefinite period of time based on the pump assembly employed, the tubing sizes, etc., employed.

If desired, the present invention can include multiple pumps infusing fluid to a patient through multiple catheters, thereby providing such fluids to the patient in volumes which are far exceed that possible by present infusers.

While the system is described herein as applicable for fluid infusion, it should be understood that the system can also be used for other purposes such as a surgical irrigation system or for autotransfusion of blood from a chest tube or cell saver.

The above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles and references referred to herein, including patents, patent applications, and publications, are incorporated herein by reference.

What is claimed is:

1. A rapid infusion system for delivery of an infusium to a patient comprising:
   a. a pump assembly;
   b. a fluid containment assembly comprising upstream conduit, downstream conduit and a self-leveling drip chamber therebetween that maintains an appropriate volume of infusium to avoid introduction of air in the downstream conduit, wherein the self-leveling drip chamber comprises:
      i. a fluid well having a top and bottom;
      ii. an inlet port in communication with the upstream conduit; and
      iii. an outlet port in communication with the downstream conduit;
   c. a vent cap in communication with the drip chamber;
   d. a means for exerting a negative pressure in the drip chamber through the vent cap;
   e. at least one fluid level sensor to detect fluid level in the fluid well; and
   f. an automated controller that receives electronic signals from the at least one fluid level sensor and sends an electronic signal to the means for exerting a negative pressure to remove air from the fluid well through the vent cap as necessary to maintain a selected fluid volume in the drip chamber.

2. The rapid infusion system of claim 1, wherein the means for exerting a negative pressure is a vacuum device.

3. The rapid infusion system of claim 2, wherein the vacuum device is a diaphragm pump in communication with the vent cap.

4. The rapid infusion system of claim 1, further comprising a check valve in communication with the vent cap to avoid egress of air from the fluid well when the means for exerting a negative pressure is inactive.

5. The rapid infusion system of claim 1, wherein the vent cap is located in the top of the fluid well.

6. The rapid infusion system of claim 1, further comprising at least one air bubble sensor to detect the presence of an air bubble in the downstream conduit, wherein the automated controller receives an electronic signal from the at least one air bubble sensor and sends an electronic signal to the pump assembly to stop delivery of infusium.

7. The rapid infusion system of claim 1, wherein the fluid containment assembly is removable.

8. The rapid infusion system of claim 1, further comprising at least one sensor to detect central venous pressure (CVP).

9. The rapid infusion system of claim 1, further comprising a heating element within the fluid containment assembly.

10. The rapid infusion system of claim 1, wherein the inlet port is in the top of the fluid well.

11. The rapid infusion system of claim 1, wherein the inlet port further comprises a curved tube to minimize introduction of air bubbles and hemolysis in the fluid well.

12. The rapid infusion system of claim 1, wherein the outlet port in the bottom of the fluid well.

13. The rapid infusion system of claim 1, wherein the bottom of the fluid well is sloped toward the outlet port.

14. The rapid infusion system of claim 1, wherein the at least one fluid level sensor is selected from an infrared, light, laser or ultrasonic sensor.

15. The rapid infusion system of claim 6, wherein the at least one air bubble sensor is selected from an infrared, light, laser or ultrasonic sensor.

16. The rapid infusion system of claim 1, wherein the fluid well is automatically maintained at approximately 50% capacity of infusium.

17. The rapid infusion system of claim 1, wherein the fluid well is automatically maintained at approximately 75% capacity of infusium.

18. The rapid infusion system of claim 1, wherein the automated controller receives an electronic signal from at least one fluid level sensor indicating a minimal fluid level and sends an electronic signal to the pump assembly to stop delivery of infusium.

* * * * *